United States Patent
Tranchina et al.

(10) Patent No.: US 10,315,030 B2
(45) Date of Patent: Jun. 11, 2019

(54) DEVICES, SYSTEMS, AND METHODS FOR IMPROVING PELVIC FLOOR DYSFUNCTION

(71) Applicant: VERESSA MEDICAL, INC., Columbus, OH (US)

(72) Inventors: Benjamin A. Tranchina, Powell, OH (US); Tracy L. Cameron, Toronto (CA); Jeffrey Richard Held, Columbus, OH (US); Jeff Weisgarber, Jewett, OH (US); Michael S. Labbe, Twinsburg, OH (US); Maekele Gebrekidan, Dublin, OH (US); Mohsin Zafar, Columbus, OH (US); Eric Gustin Hassenpflug, Westerville, OH (US); Alexandru Campean, Strongsville, OH (US); Robert K. Deckman, San Bruno, CA (US); Steven E. Wilder, Blacklick, OH (US)

(73) Assignee: VERESSA MEDICAL, INC., Columbus, OH (US)

( * ) Notice: Subject to any disclaimer, the term of this patent is extended or adjusted under 35 U.S.C. 154(b) by 0 days.

(21) Appl. No.: 15/873,290

(22) Filed: Jan. 17, 2018

(65) Prior Publication Data

US 2018/0200516 A1 Jul. 19, 2018

Related U.S. Application Data

(60) Provisional application No. 62/580,540, filed on Nov. 2, 2017, provisional application No. 62/506,814, filed (Continued)

(51) Int. Cl.
*A61N 1/36* (2006.01)
*A61N 1/372* (2006.01)
(Continued)

(52) U.S. Cl.
CPC ........ *A61N 1/36007* (2013.01); *A61B 5/0488* (2013.01); *A61B 5/6847* (2013.01); (Continued)

(58) Field of Classification Search
CPC ............ A61N 1/36007; A61N 1/36107; A61N 1/37005; A61N 1/37518
See application file for complete search history.

(56) References Cited

U.S. PATENT DOCUMENTS

| 5,284,153 A | 2/1994 | Raymond et al. |
| 5,775,331 A | 7/1998 | Raymond et al. |

(Continued)

FOREIGN PATENT DOCUMENTS

WO WO2016028608 A1 2/2016

OTHER PUBLICATIONS

PCT International Search Report and Written Opinion for corresponding International Application No. PCT/US2018/014019, dated May 28, 2018, pp. 1-11.

*Primary Examiner* — Tammie K Marlen
(74) *Attorney, Agent, or Firm* — Tarolli, Sundheim, Covell & Tommino LLP

(57) ABSTRACT

Methods, devices and systems for improving pelvic floor dysfunction in a patient suffering therefrom by electrically modulating neural tissue in a minimally invasive fashion using an electrical microstimulator are provided. Methods include inserting an electrical microstimulator having a re-deployable fixation member through skin of a patient's leg and advancing the electrical microstimulator through the skin along tissue of a surgical pathway to an area of the patient's leg. A target implant site can be identified that is above deep fascia and below the skin and that is adjacent to a target nerve associated with pelvic floor function. The electrical microstimulator can be anchored to the target (Continued)

implant site via the re-deployable fixation member or re-positioned, if necessary. A therapy electrical signal can be delivered to the target nerve from the target implant site.

19 Claims, 19 Drawing Sheets

Related U.S. Application Data on May 16, 2017, provisional application No. 62/446,983, filed on Jan. 17, 2017.

(51) Int. Cl.
*A61N 1/375* (2006.01)
*A61B 5/0488* (2006.01)
*A61B 5/00* (2006.01)

(52) U.S. Cl.
CPC ..... *A61N 1/36071* (2013.01); *A61N 1/36107* (2013.01); *A61N 1/36139* (2013.01); *A61N 1/37205* (2013.01); *A61N 1/37518* (2017.08); *A61B 5/7264* (2013.01); *A61N 1/36103* (2013.01); *A61N 1/36132* (2013.01)

(56) References Cited

U.S. PATENT DOCUMENTS

| | | |
|---|---|---|
| 6,366,814 B1 | 4/2002 | Boveja |
| 6,466,817 B1 | 10/2002 | Kaula et al. |
| 6,907,295 B2 | 6/2005 | Gross et al. |
| 7,177,698 B2 | 2/2007 | Klosterman et al. |
| 7,214,197 B2 | 5/2007 | Prass |
| 7,444,180 B2 | 10/2008 | Kuzma et al. |
| 8,050,769 B2 | 11/2011 | Gharib et al. |
| 8,052,688 B2 | 11/2011 | Wolf, II |
| 8,244,377 B1 | 8/2012 | Pianca et al. |
| 8,532,790 B2 | 9/2013 | Griswold |
| 8,655,451 B2 | 2/2014 | Klosterman et al. |
| 8,774,924 B2 | 7/2014 | Weiner |
| 8,801,626 B2 | 8/2014 | Sun et al. |
| 9,044,592 B2 | 6/2015 | Imran et al. |
| 9,398,901 B2 | 7/2016 | Tischendorf et al. |
| 9,533,141 B2 | 1/2017 | Black et al. |
| 9,585,642 B2 | 3/2017 | Dinsmoor et al. |
| 9,610,442 B2 | 4/2017 | Yoo et al. |
| 9,636,498 B2 | 5/2017 | Leven |
| 9,643,003 B2 | 5/2017 | Yu |
| 9,656,074 B2 | 5/2017 | Simon et al. |
| 2007/0066997 A1* | 3/2007 | He .................. A61N 1/372 607/3 |
| 2007/0265675 A1 | 11/2007 | Lund et al. |
| 2010/0249643 A1 | 9/2010 | Gozani et al. |
| 2011/0288618 A1 | 11/2011 | Glen et al. |
| 2012/0323253 A1 | 12/2012 | Garai et al. |
| 2013/0289659 A1 | 10/2013 | Nelson et al. |
| 2014/0081366 A1 | 3/2014 | Bentley et al. |
| 2014/0163580 A1* | 6/2014 | Tischendorf ........ A61N 1/36139 606/129 |
| 2014/0378941 A1 | 12/2014 | Su et al. |
| 2015/0148878 A1 | 5/2015 | Yoo et al. |
| 2016/0023005 A1* | 1/2016 | Perryman .......... A61N 1/37229 607/60 |
| 2016/0263376 A1 | 9/2016 | Yoo et al. |
| 2016/0339239 A1 | 11/2016 | Yoo et al. |
| 2017/0173328 A1* | 6/2017 | Ostroff .............. A61N 1/36007 |
| 2017/0304614 A1 | 10/2017 | Yoo et al. |
| 2017/0361093 A1 | 12/2017 | Yoo et al. |
| 2018/0078760 A1* | 3/2018 | Lee .................. B23K 26/40 |

* cited by examiner

DEVICES, SYSTEMS, AND METHODS FOR IMPROVING PELVIC FLOOR DYSFUNCTION

RELATED APPLICATIONS

The present application claims priority to U.S. Provisional Application No. 62/580,540, filed on Nov. 2, 2017, which claims priority to U.S. Provisional Application No. 62/446,983 filed on Jan. 17, 2017 and U.S. Provisional Application No. 62/506,814 filed on May 16, 2017, the entirety of all applications incorporated by reference in their entirety. This application also relates to co-pending application Ser. No. 15/873,323, entitled: "Devices, Systems, and Methods for Identifying a Target Implant Site," filed on Jan. 17, 2018, the entirety of which is incorporated by reference herein.

TECHNICAL FIELD

The present disclosure relates to electrical microstimulators, delivery systems for implanting electrical microstimulators, and methods of improving pelvic floor dysfunction and peripheral nerve pain.

BACKGROUND

Overactive bladder (OAB), a type of pelvic floor disorder, is a symptom complex that is characterized by urinary urgency, with or without urgency-associated urinary incontinence. OAB is often associated with urinary frequency and nocturia in the absence of infection or other obvious pathology.

Current treatment options for OAB include behavioral therapy, pharmacotherapy, and neuromodulation. Behavioral therapies include lifestyle changes, bladder training, and pelvic floor muscle training. Pharmacological agents approved for use in OAB include anticholinergics, beta3-receptor agonists and detrusor injections of neuromuscular blockers. Anticholinergics inhibit the binding of acetylcholine to the muscarinic receptors in the detrusor muscle, thereby suppressing involuntary bladder contractions. This results in an increase in bladder volume voided and a decrease in micturition frequency, sensation of urgency, and the number of urge incontinence episodes. Beta3 adrenergic agonists elicit a direct inhibition of afferent nerve firing independent of the relaxing effects on bladder smooth muscle. Detrusor injections of botulinum neurotoxin type A, a neuromuscular blocker, may be considered for adults with OAB who cannot use or do not adequately respond to anticholinergic medication.

In terms of neuromodulation, the two most commonly utilized techniques are sacral nerve stimulation (SNS) and percutaneous tibial nerve stimulation (PTNS). SNS provides continuous stimulation of the sacral nerve through surgical implantation of a permanent electrode and a permanent pulse generator while PTNS uses intermittent stimulation of the tibial nerve at the ankle with no permanently implanted lead or stimulator. SNS procedures involve making a midline sacral incision and carrying the incision down to the level of the lumbodorsal fascia, which is opened sharply from the midline. The underlying paravertebral muscles are separated or divided, and the sacral periosteum is identified. An electrical lead is ultimately inserted through the appropriate sacral foramen to lie adjacent to the sacral nerve and the lead is sutured to the periosteum to prevent lead migration. An example of PTNS involves percutaneously inserting a fine-gauge needle just above the ankle next to the tibial nerve and placing a surface electrode on the foot. The needle and electrode are connected to a low-voltage stimulator that delivers stimulation pulses to the tibial nerve. PTNS therapy is provided in an outpatient clinic setting and, in general, is performed initially for 30 minutes weekly for 12 weeks, followed by occasional treatments as needed based on patient symptoms. An advantage of SNS and PTNS is that the electrode is placed close to the target nerve providing direct stimulation of the nerve and requiring less energy consumption.

Recent studies have also been carried out regarding the efficacy of transcutaneous tibial nerve stimulation with the use of external electrodes. Electrodes are applied near to the ankle where the tibial/sural nerve is located. It is believed that the electrical stimulation can penetrate the skin delivering tibial nerve stimulation in the same way as PTNS, but without the need for a needle electrode. Transcutaneous tibial nerve stimulation is completely non-invasive, with surface electrodes connected to a battery operated stimulator and applied to an appropriate site of the body. Such treatment generally does not require regular patient visits at clinics and usually is self-administered at home, which is convenient for the patient.

SUMMARY

The present disclosure generally relates to methods and devices for improving pelvic floor dysfunction in a patient suffering therefrom by electrically modulating neural tissue in a minimally invasive fashion using an electrical microstimulator (also referred to herein as a "microstimulator"). Devices, systems and methods can also be used for peripheral nerve stimulation to treat peripheral nerve pain, for example.

In an embodiment, a method of improving pelvic floor dysfunction in a patient suffering therefrom comprises inserting a microstimulator through skin of a patient's leg and advancing the microstimulator to an area of the patient's leg. The microstimulator includes a re-deployable fixation member. The method further includes positioning the microstimulator at a target implant site adjacent to a target nerve associated with pelvic floor function. In certain embodiments, the target implant site is above deep fascia and below the skin. The method further comprises anchoring re-deployable fixation member of the microstimulator to the target implant site. Once the microstimulator has been anchored to the target implant site, the method comprises delivering a therapy electrical signal to the target nerve to improve pelvic floor dysfunction.

DETAILED DESCRIPTION

The present disclosure generally relates to methods, devices and systems for improving pelvic floor dysfunction in a patient suffering therefrom by electrically modulating neural tissue in a minimally invasive fashion using an electrical microstimulator. A "microstimulator" as used herein has a width of greater than 0 mm and less than approximately 7 millimeters (mm), a height of greater than 0 mm and less than approximately 6 mm and a length of greater than 0 mm and less than approximately 30 mm.

As used herein with respect to a described element, the terms "a," "an," and "the" include at least one or more of the described element including combinations thereof unless otherwise indicated. Further, the terms "or" and "and" refer to "and/or" and combinations thereof unless otherwise indicated. It will be understood that when an element is referred to as being "over," "on," "attached" to, "connected" to, "coupled" with, "contacting," "in communication with," etc., another element, it can be directly over, on, attached to, connected to, coupled with, contacting, or in communication with the other element or intervening elements may also be present. In contrast, when an element is referred to as being "directly over," "directly on," "directly attached" to, "directly connected" to, "directly coupled" with, "directly contacting," or in "direct communication" with another element, there are no intervening elements present. An element that is disposed "adjacent" another element may have portions that overlap or underlie the adjacent element. By "substantially" is meant that the shape, configuration, or orientation of the element need not have the mathematically exact described shape, configuration or orientation but can have a shape, configuration or orientation that is recognizable by one skilled in the art as generally or approximately having the described shape, configuration, or orientation.

Figure 1:
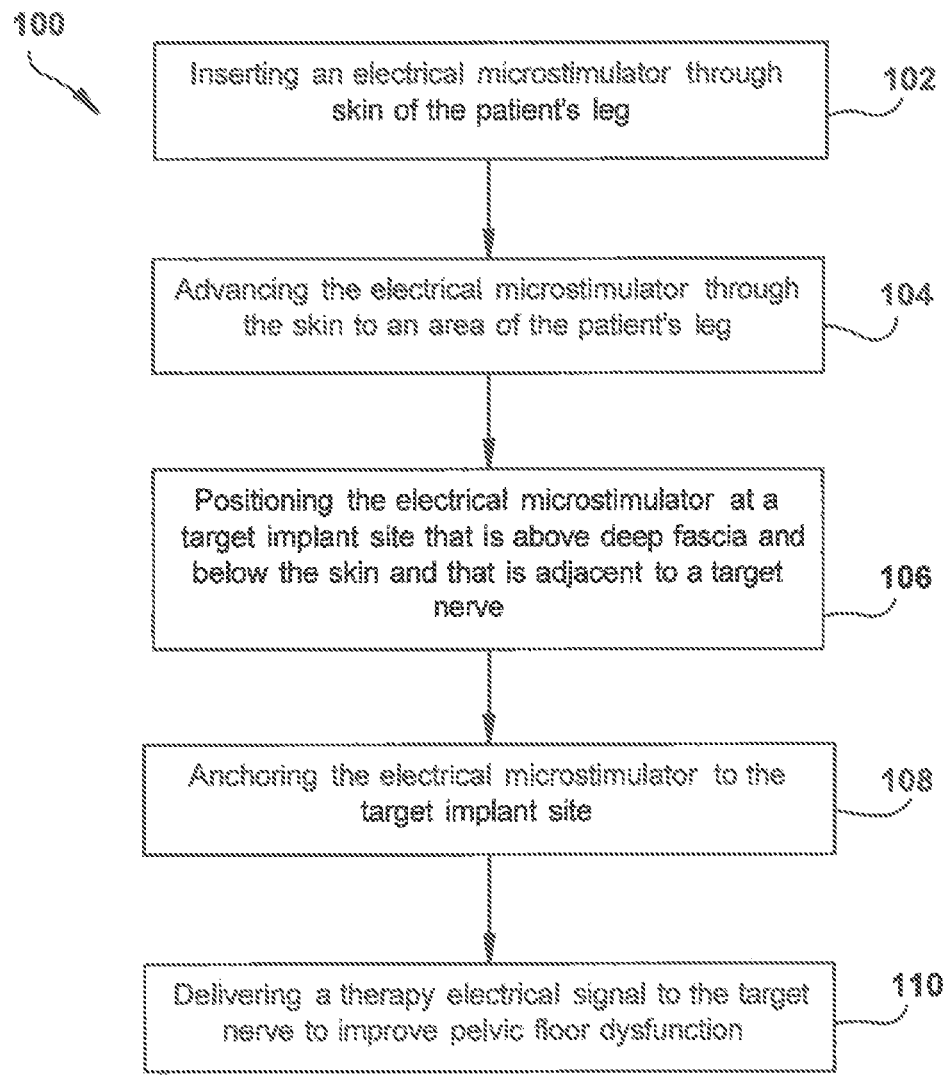
FIG. 1 is a flow diagram indicating steps of a method of improving pelvic floor dysfunction according to an embodiment of the present disclosure.
Figure 4:
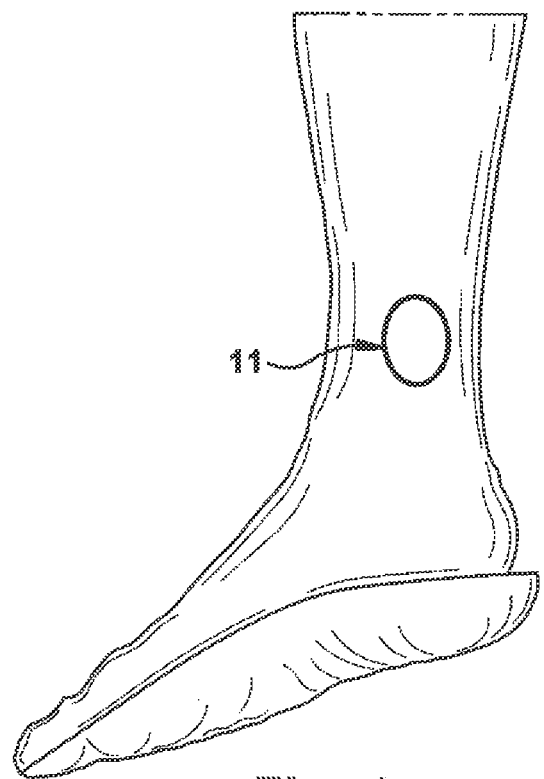
FIG. 4 is a schematic illustration of the lower portion of a patient's leg indicating a region to which a microstimulator can be implanted according to an embodiment of the present disclosure.

Referring to FIG. 1, in an embodiment, a method (100) of improving pelvic floor dysfunction can comprise inserting a microstimulator through skin of a patient's leg (step 102) and advancing the micro stimulator to an area of the patient's leg (step 104). The microstimulator has a re-deployable fixation member as described in more detail below. The area of the patient's leg can be on the medial side of the patient's leg below or at the knee and posterior to the tibia; or immediately below or at the medial condyle of the tibia. The microstimulator can be advanced to region 11 as illustrated in FIG. 4. Method 100 can further include positioning the microstimulator at a target implant site adjacent to a target nerve associated with pelvic floor function (step 106). In certain embodiments, the target implant site is above deep fascia and below the skin. Method 100 can further comprise anchoring re-deployable fixation member of the microstimulator to the target implant site (step 108). In certain embodiments, the microstimulator is anchored above deep fascia and not to a layer of deep fascia (such as not affixing the microstimulator to the superficial surface of the deep fascia tissue layer). Once the microstimulator has been anchored to the target implant site, method 100 can comprise delivering a therapy electrical signal to the target nerve to improve pelvic floor dysfunction (step 110). The therapy electrical signal can modulate the target nerve by increasing or decreasing neuronal activity. As such, the therapy electrical signal can be an excitatory or inhibitory stimulation signal or a combination thereof. The therapy electrical signal may also mask, alter, override, or restore neuronal activity.

Figure 2:
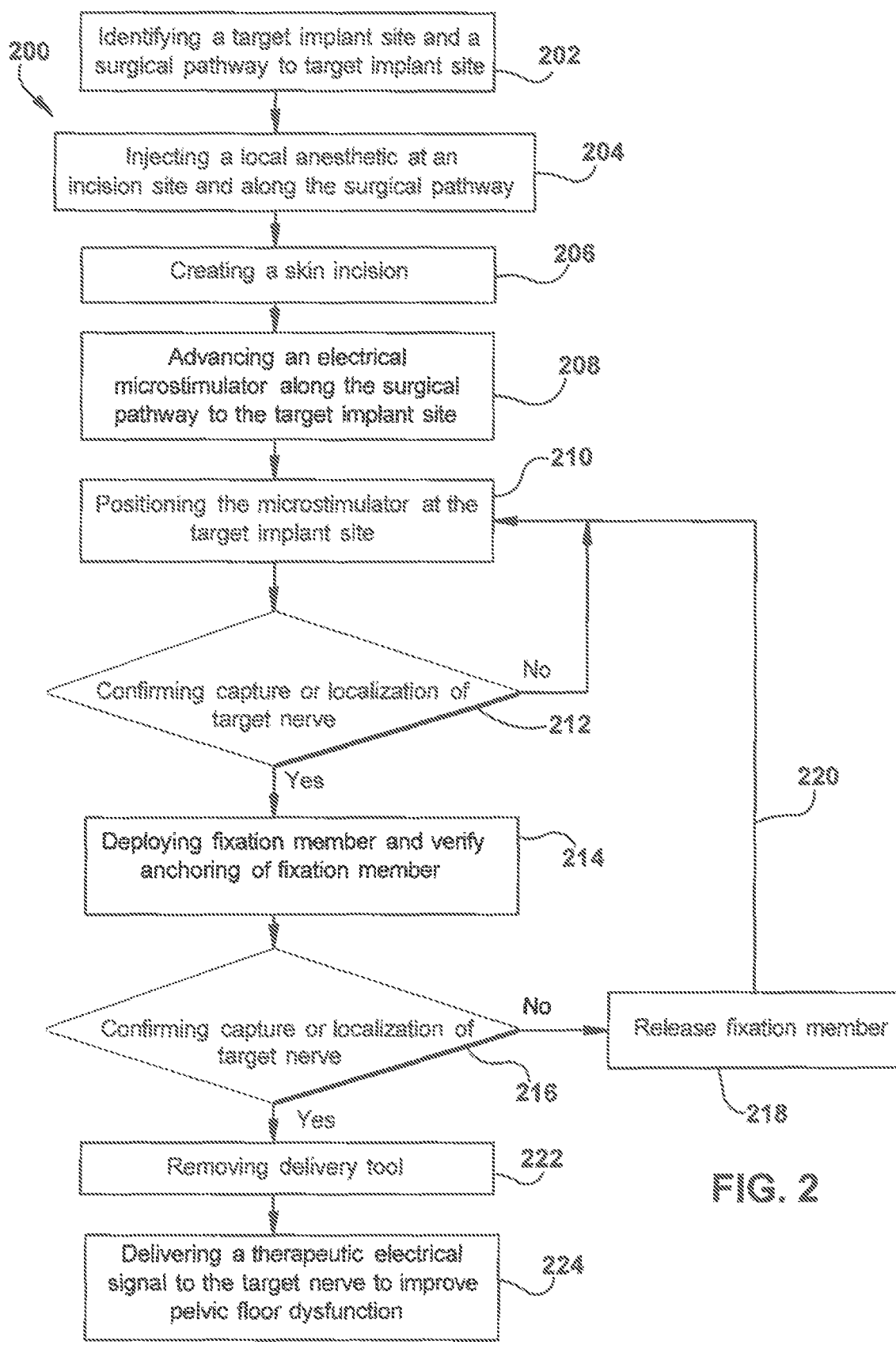
FIG. 2 is a flow diagram indicating steps of a method of improving pelvic floor dysfunction according to an embodiment of the present disclosure.

Referring to FIG. 2, in an additional or alternative embodiment, a method of improving pelvic floor dysfunction (200) can comprise identifying a target implant site to implant the microstimulator and a surgical pathway to reach the target implant site (step 202). The target implant site is adjacent to a target nerve associated with pelvic floor function. The target implant site can be determined, for example, using ultrasound, external skin electrodes, anatomical landmarks, or other imaging or stimulating techniques. Visualization or localization of the target nerve as an initial step can be used to guide a clinician in selecting an incision site. After locating the target implant site and the surgical pathway to the target implant site, method 200 can comprise injecting a local anesthetic at an incision site and along the pathway to the target implant site (step 204). This can be done by inserting a syringe to the implant target location along the pathway to the implant target location and slowly injecting anesthetic while removing the syringe, or with a syringe with multiple exit ports along the length that distribute anesthetic along the entire pathway.

At step 206, a skin incision can be created. In particular and with additional reference to FIG. 5, microstimulator 10 can be inserted through skin tissue by incising outer skin layer 12 using, for example, a standard scalpel or an incising edge or blade of a delivery tool. The incision is preferably minimal in size to tightly accommodate microstimulator 10. For example, the length of the skin incision can be approximately equal to the width of an incising end of a delivery tool to provide an incision just large enough to insert microstimulator 10 or the distal end of delivery tool 20 used to deploy microstimulator 10.

Figure 5:
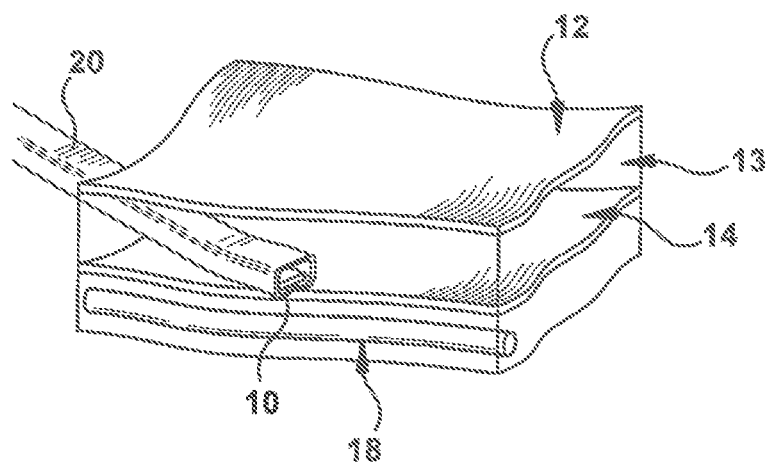
FIG. 5 is a schematic illustration of a site in connective tissue below skin and above deep fascia where a delivery tool can be advanced and a microstimulator positioned according to an embodiment of the present disclosure.

At step 208, method 200 can comprise advancing the microstimulator along the surgical pathway to the target implant site. As illustrated in FIG. 5, microstimulator 10 can be inserted and advanced subdermally via delivery tool 20 to the target implant site. The delivery tool can have a flexible tip and/or a blunt tip (as described in more detail below) so that it can be advanced at a shallow angle until deflected by deep fascia layer 14 and thereby to the target implant site that is above deep fascia layer 14 as schematically illustrated in FIG. 5. Such a flexible and/or blunt tip of the microstimulator can allow placement of the microstimulator as close as possible to the deep fascia while remaining within the safest tissue region. Other ways in which deep fascia can be detected and/or avoided are described below. When a delivery tool advances a microstimulator through tissue above deep fascia, a tunnel is created such that a tissue pocket extends in the patient's tissue from the incision site to the target implant site. Such a tunnel can be filled leaving only a tight pocket within which the microstimulator can reside. The tissue pocket can be just large enough to receive the microstimulator. The tunnel can be filled with a collagen matrix, gel or similar material. Such a material can contain wound or tissue repair substances to facilitate tissue healing. The tunnel can additionally or alternatively be mechanically pinched together and closed using a stitch, clip, staple or other closure device.

With further reference to FIG. 5, method 200 can further include positioning microstimulator 10 at the target implant site (step 210). As mentioned above, the target nerve is a nerve associated with pelvic floor function. In certain embodiments, the target implant site is above deep fascia 14 adjacent to a target nerve, such as target nerve 18. Exemplary target nerves are tibial nerve 18 (including the posterior tibial nerve), a saphenous nerve, a cutaneous branch of the tibial nerve, a cutaneous branch of the saphenous nerve, or combinations thereof. The target nerve can be two or more nerves and as used herein "a target nerve" can include a plurality of nerves. In certain embodiment, a target nerve is the tibial nerve (or a cutaneous branch of the tibial nerve) and the saphenous nerve (or a cutaneous branch of the saphenous nerve).

Figure 3:
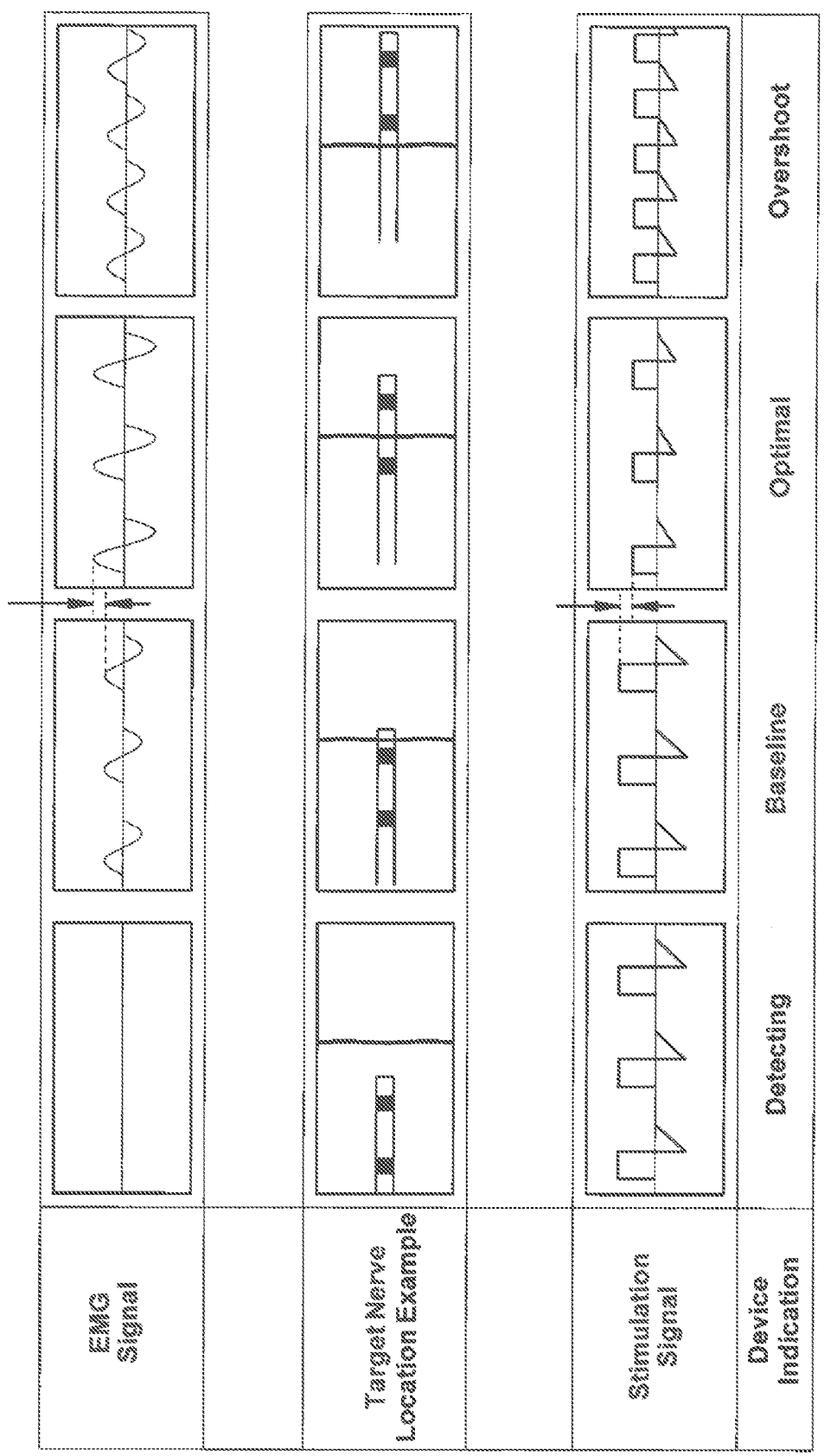
FIG. 3 depicts schematic illustrations of EEG signals corresponding to stimulation signals that are applied by a microstimulator or delivery tool as the microstimulator is being inserted through tissue according to an embodiment of the present disclosure.

Regarding step 212, capture or localization of the target nerve can be confirmed. For example, using either electrodes located on the microstimulator, separate electrodes on the delivery tool (also referred to as an "insertion tool" herein), and/or transcutaneous (surface) electrodes, electrical stimulation can be performed and activation of the target nerve can be sensed. Sensing can be performed by external sensors monitoring ENG, EMG, or evoked potentials activity; or patient movement. For example, stimulation electrodes on the tip of the delivery tool can evoke action potentials in the tibial nerve that are measured via an EMG as a muscle reflex on the sole of the foot. The sensors can be placed anywhere on the patient's body that is innervated by the target nerve. For instance, the sensors can alternatively be placed on the sole of the patient's foot to detect EMG activity of the Flexor hallucis brevis, Flexor digitorum brevis, or Flexor digiti minimi brevis of the foot, for example. As the delivery tool is inserted and advanced through tissue, the sensors can continuously sense EMG activity of a muscle innervated by the target nerve as stimulation pulses are delivered by the stimulation electrodes. Detection of a maxima (a maxima is the maximum value of a signal that occurs within a function of a given algorithm and not necessarily the maximum signal possible) in ENG, EMG, or evoked potentials activity indicates that the microstimulator is most proximate to the target nerve. Such a location when accomplished at the lowest strength of the stimulation pulse (e.g. amplitude) achieves an implant procedure that causes the least patient discomfort, and results in an implant site that provides therapeutic stimulation at the lowest power consumption requirements. In other words, a method can employ an algorithm that determines nerve capture so that when an ENG, EMG, or evoked potential signal is detected, the stimulation strength can be commensurately adjusted to find an implant site where a maxima in ENG, EMG, or evoked potential signal is elicited with minimal stimulation pulse strength. By dynamically adjusting the balance between an ENG, EMG, or evoked potential signal and stimulus strength, the target implant site can be determined while avoiding a painful motor or sensory response from the patient, such as a painful muscle contraction. FIG. 3 provides a schematic illustration of a microstimulator moving towards a target nerve and the corresponding stimulation signal applied by electrodes, the corresponding EMG signal, and the corresponding indication on the device or insertion tool regarding the EMG signal ("Detecting;" "Baseline;" "Optimal;" and "Overshoot") described in more detailed below.

Regarding transcutaneous stimulation to localize a target nerve, such a method can be used in addition to or instead of the target nerve localization steps described above. For example, EMG recording electrodes can be applied to a portion of the patient's body innervated by the target nerve. For example, if the target nerve is the tibial nerve, the EMG electrodes can be applied to the bottom of the patient's foot adjacent to the abductor hallucis muscle on the bottom of the patient's foot. Stimulation pulses can be applied, via transcutaneous electrodes, to a portion of the patient's body adjacent to the target nerve. For example, if the target nerve is the tibial nerve, transcutaneous electrodes can be placed on the patient's ankle. An EMG signal can be detected via the recording electrodes. Detection of an EMG signal can indicate that the target nerve has been localized and the target medical device implant site has been identified. A mechanical template can be used to mark a tunneling path and incision point. An appropriate skin incision can then be made and an insertion tool can be inserted through the incision towards the target medical device implant site. Once the target medical device implant site has been reached, the microstimulator can be released from the insertion tool and anchored to the medical device implant site.

Figure 2A:
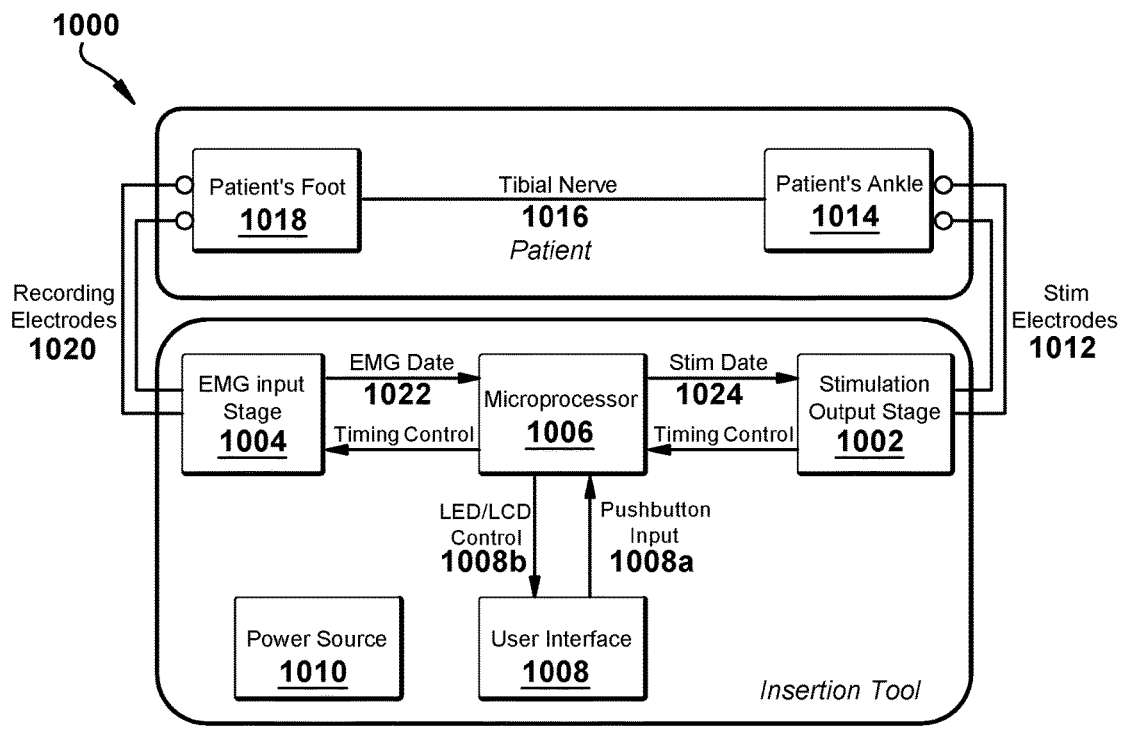
FIG. 2A is a block diagram of exemplary components of a system according to an embodiment of the present disclosure.

An exemplary system that can be used to localize a target nerve, including transcutaneous stimulation, is provided in FIG. 2A. Insertion tool 1000 includes a stimulation output stage 1002 and an evoked potential input stage, such as EMG input stage 1004, a microprocessor 1006, a user interface 1008 and a power source 1010. Although the stimulation output stage is illustrated as being a part of the insertion tool, it can also be part of the microstimulator. To perform nerve localization, the microprocessor can send a control signal to the stimulation output stage to send a stimulation pulse to the patient's tissue via stimulation electrodes 1012. Such stimulation electrodes can be placed on the patient's ankle 1014 for example. If the electrodes are in the vicinity of the target nerve, such as the tibial nerve 1016, an action potential will be created that travels along the tibial nerve to a muscle in the patient's foot 1018 innervated by the tibial nerve, such as the abductor hallucis muscle, for example. EMG recording electrodes 1020 can be placed on the surface of the skin above the abductor hallucis muscle, for example. The EMG input stage 1004 can sample raw EMG data 1022 for a short period of time (such as, for example, approximately 16 microseconds) after the end of each stimulation pulse. The raw EMG data can then be analyzed by the microprocessor to first determine whether an EMG signal is present, and if it is, to also determine the strength of the EMG signal. Using information about the EMG that resulted from a previous stimulation pulse, the microprocessor can adjust the parameters for the next stimulation pulse 1024. The user interface, which can include pushbuttons 1008a, LED/LCD indicators 1008b, and or audio inputs and outputs, can also be updated to reflect the status of nerve localization.

The EMG input stage, for example, can use an analog front end integrated circuit with a 24-bit analog-to-digital circuit that can be set to approximately 4,000 or 8,000 samples per second, for example. The raw EMG signals can be processed using fast fourier transform (FFT) to measure the presence and strength of the EMG signal. This can allow pulse-by-pulse control of the stimulation, which adds to the robustness of the nerve localization methodology.

Figure 2B:
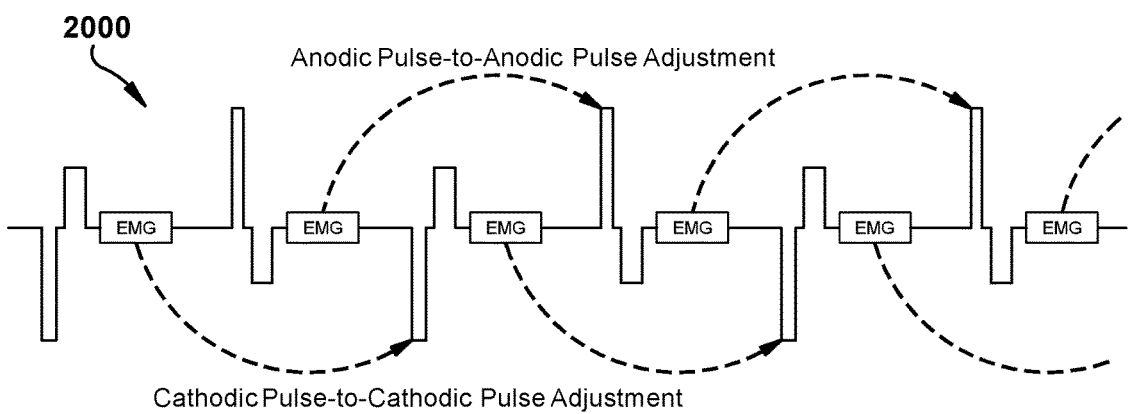
FIG. 2B is a schematic illustration of a stimulation profile for nerve localization according to an embodiment of the present disclosure.

A relevant aspect of nerve localization can be the stimulation profile. For example, the angle-of-approach to the target nerve can have an impact on the ability to recruit the target nerve, such as the tibial nerve. For example, without wishing to be bound by theory, certain angles-of-approach may hyperpolarize a region of the tibial nerve (as opposed to the desired depolarization), potentially blocking action potentials from traveling to the abductor hallucis muscle. To avoid this possible issue and to allow the nerve localization to work robustly regardless of the angle-of-approach, an insertion tool can be used with the stimulation profile 2000 depicted in FIG. 2B. As can be seen from this figure, the polarity of stimulation is alternated from pulse to pulse. This means that if hyperpolarization is blocking action potentials during a cathodic pulse, the change in polarity for the next anodic pulse should prevent hyperpolarization in the same region, allowing action potentials to pass. The stimulation profile illustrated in FIG. 2B can be used for various ways of localizing a nerve as described herein and is not limited to nerve localization via transcutaneous stimulation.

Transcutaneous nerve localization, as disclosed herein, can provide several advantages compared to other neural recording systems. For example, most neural recording systems use blanking, amplification, filtering, and/or averaging to measure EMG signals. An insertion tool, as described above, does not necessarily require such techniques. Instead, disclosed methods can involve collecting raw EMG data using one channel of input and a 24-bit analog-to-digital converter, for example. The data collection occurs during a short window of time (such as, for example, approximately 16 milliseconds) after each pulse. When the target nerve is the tibial nerve, low-level EMG signals can be detected at the surface of the foot even before a toe twitch is elicited. In addition, this technique is so fast that it can allow the stimulation parameters to be adjusted before the next pulse, meaning that the nerve localization methodology can be fast and extremely responsive.

The EMG processing technique, as described above, is also different from other neural recording systems. For example, raw EMG data can be processed using FFT with no pre-processing. Post-processing integration of the FFT results can also produce a single number that indicates the strength of the EMG signal. For example, integrating the FFT results between 125-500 Hz can provide a reliable measure of the EMG strength. This is useful for several reasons. For example, it provides EMG strength feedback when determining how well the EMG recording electrodes are placed on the foot, for example. Further, it provides useful information during nerve localization when trying to keep the EMG response from toe twitch, for example, to a minimum.

The pulse-by-pulse control during nerve localization also provides advantages. For example, as the clinician is tunneling the insertion tool towards the target nerve, such as the tibial nerve, the nerve localization methodology preferably responds as quickly and robustly as possible. The clinician needs instant feedback as the tool approaches the nerve, since distances as small as a few millimeters can have a large effect on nerve response. Given the methodology described herein, it is possible to do pulse-by-pulse control with stimulation frequencies as high as 50 Hz, for example.

Pulse-by-pulse control is also relevant to minimize the impact on the patient since a goal of therapy is for the patient to feel as little pain as possible during the implant procedure or during localization of the target implant site. As the insertion tool, as described herein, approaches the target nerve, such as the tibial nerve, it is preferable to turn down the stimulation amplitude as quickly as possible to reduce the amount of afferent (sensory) fibers that are activated. In addition, it is preferably to minimize the amount of toe twitch in the case of tibial nerve stimulation, for example. Not only can toe twitch be uncomfortable for the patient, the movement can make it more difficult for the clinician to tunnel the insertion tool accurately.

As described above, for tonic stimulation, the angle at which the insertion tool is tunneled towards the nerve can make a difference in the ability to recruit the target nerve. Therefore, it has been determined as disclosed herein that a stimulation profile that alternates the polarity of the pulse from one pulse to the next is preferable. This means that if action potentials are being blocked for one polarity, the action potentials will not be blocked during the subsequent pulse.

Transcutaneous nerve localization has several additional advantages. During the implant procedure, transcutaneous nerve localization can be used to identify the target location for the microstimulator or the target medical device implant site prior to creating a stab incision. This may provide more confidence than simply using a mechanical template to identify the target implant site. A transcutaneous method can also be used as a simple trial to determine whether a patient is a candidate for an implant. Further, a transcutaneous method can be used to identify ideal electrode locations for a surface stimulator that could be used instead of an implant. Transcutaneous nerve localization can be used for many applications unrelated to tibial nerve stimulation, which has only been provided as an exemplary embodiment. For example, it could be used to maps nerves prior to surgery, allowing doctors to mark areas to avoid while cutting.

Moreover, methodologies as described herein are in contrast to other types of nerve localization methods where EMG signals are measured while a patient is under general anesthesia, in which case, a clinician is not necessarily concerned with a patient perceiving pain. In such instances, a magnitude of stimulation strength is applied to recruit a target nerve, with no regard to the number of motor units (a motor unit is made up of a motor neuron, and the muscle fibers innervated by that motor neuron's axonal terminals) activated, power consumption by stimulating electrodes, or proximity of stimulating electrodes to the target nerve. In forms of PTNS, a clinician can ramp up the strength of stimulation until achieving a motor response in the patient's big toe or the bottom of the patient's foot, for example. The clinician then reduces the strength of the stimulation to obtain a therapeutic delivery signal. In certain methods as disclosed herein, a target nerve is localized before the patient experiences any undesirable or uncomfortable motor or sensory responses and, preferably, a minimum number of motor units, are recruited and detected via an EMG. In certain methods as disclosed herein, target nerves can comprise mixed nerves (nerves with both motor and sensory axons), pure motor, or pure sensory nerves. Such a methodology is also different from other nerve localization techniques where the clinician is trying to achieve an implant location with a delivery tool or the implantable device by either getting as proximate to a target nerve as possible or avoiding contact with a target nerve. Methodologies as disclosed herein can locate a target nerve while remaining a safe distance from the target nerve.

Referring again to FIG. 2, at step 214, a delivery tool can deploy a fixation member (as described in more detail below) to anchor the microstimulator at the target implant site, which can be connective tissue above deep fascia. Sufficient anchoring can be verified, for example, by gently pulling the delivery tool to test the strength of the anchor, or by force measurement confirming adequate microstimulator resistance to movement is obtained (as described in more detail below). For example, to ensure that the microstimulator is securely anchored, the delivery tool or a portion of the delivery tool can be retracted proximally to determine if the fixation member disengages from the target implant site. If so, the fixation member can be released and re-deployed until it is determined that the microstimulator is securely anchored to the target implant site. The microstimulator can be positioned parallel, perpendicular or at any angle to the target nerve.

At step 216, sufficient nerve capture confirmation is performed, as described in step 212. Nerve capture confirmation can be achieved by delivering test stimulation pulses and measuring and/or observing a stimulation response. If the proper stimulation location and anchoring strength is verified, the microstimulator can be released and the delivery tool can be removed (step 220). Alternatively, if the stimulation location and anchoring strength are not adequate, the fixation member can be released (disengaged from tissue) (step 220) and the delivery tool can reposition the microstimulator (step 222). Steps 210 through 216 can be performed until sufficient stimulation and anchoring are achieved.

Once sufficient stimulation and anchoring are achieved at step 216, the microstimulator can be released or "undocked" from the delivery tool (as described in more detail below) and the delivery tool can be removed (step 222). In certain embodiments, prior to release of the microstimulator, the microstimulator can be programmed to deliver a stimulation signal having pre-determined parameters, such as a pre-determined intensity, that are deemed to have therapeutic benefits. The patient's response to such stimulation can be observed or detected for any painful or uncomfortable response. Gauging the sensation perceived by the patient before releasing the microstimulator from the delivery tool can increase the probability of prescribed therapy compliance and decrease adverse effects due to stimulation. At step 224, the microstimulator can deliver a therapeutic electrical signal to the target nerve to improve pelvic floor dysfunction.

The above described methods are exemplary and other methods for implanting a microstimulator to deliver a therapy signal to a target nerve to improve pelvic floor dysfunction can include combinations and sub-combinations of the above-described steps, including the elimination or addition of certain steps.

In certain methods of improving pelvic floor dysfunction as disclosed herein, a microstimulator can be implanted in a target implant site that is above deep fascia adjacent to a target nerve associated with pelvic floor function. Compared to SNS and PTNS procedures for treating overactive bladder (OAB), certain methods as disclosed herein involve implanting a microstimulator further away from a target nerve and anchoring the microstimulator in randomly distributed connective tissue. For example, SNS and PTNS involve implanting or inserting an electrode directly adjacent to the target nerve and therefore such procedures have a greater probability of activating the target nerve. However, methods and devices disclosed herein can deliver an efficacious electrical therapy signal to the target nerve and can also securely and safely fixate the microstimulator to looser connective tissue of the target implant site that is above deep fascia.

Regarding delivering an efficacious electrical therapy signal, electrical current delivered by the microstimulator can be steered to shape the stimulation field to ensure appropriate nerve capture. For example, a microstimulator can be used that has independently programmable electrodes that can each be activated, deactivated, programmed to deliver a certain percentage of electrical current, and/or have independent current sources (stimulation channels) to customize, shape and steer the electrical current. Independently programmable electrodes also allow the modulation to be directional in nature applying an activation signal to only certain regions while sparing modulation to others. Such directional electrodes allow for precise selective modulation of the target nerve as well as allow steering of the electrical signal. Independently programmable electrodes also allow simultaneous or sequential delivery of electrical signals to one or more target nerves with each electrical signal having stimulation parameters, such as frequency, amplitude, pulse width, specific to the target nerve to maximize therapy. A set of specific values for each stimulation parameter can constitute a program (for example 2 Hz, 10 mA, 50 ms respectively). Further, the microstimulator can be programmed to deliver at least two independent stimulation programs to the target nerve.

In addition to modulating the direction of the electrical signal, the degree of activation that each electrode delivers can be adjusted. For example, the pulsing parameters of electrodes may be adjusted to initiate, stop, increase, or decrease the pole combinations, energy, amplitude, pulse width, waveform shape, frequency, and/or voltage or other pulsing parameter to adjust the degree of modulation delivered thereby. Additionally, the shape of the electric field can vary corresponding to the power applied, the number and arrangement of electrodes, and particular shapes and sizes chosen for the electrodes. For example, the electrodes can be ring-shaped or can be segmented electrodes that do not extend 360° about the microstimulator body.

Furthermore, each electrode may be selectively powered as an anode, cathode. For example, a microstimulator can have any combination of cathodes and anodes (as long as there is at least one cathode and at least one anode) thereby providing different shaped current fields. Alternatively, a microstimulator can be programmed such that only one pair of electrodes is active at any given time, limited to either a top pair of electrodes or a bottom pair of electrodes. Further, the electrodes can be sufficiently spaced apart to allow independent current settings for each of the electrodes of the microstimulator. In certain embodiments, electrodes are positioned on the two widest portions of a microstimulator have a top surface and a bottom surface. The electrodes on the bottom surface will be facing towards the fascia and tibial nerve and the electrodes on the top surface will be facing towards the skin and cutaneous saphenous branches. In certain embodiments, a microstimulator can include an Application Specific Integrated Circuit (ASIC) to provide current steering.

In certain embodiments, a microstimulator has two electrodes in total located on the bottom surface of the microstimulator body. In other embodiments, the microstimulator has four electrodes in total, electrodes positioned on each of the top and bottom surfaces. In one embodiment, each stimulation pulse is either between an anode and cathode on the top surface or an anode and cathode on the bottom surface. In another embodiment, each stimulation pulse can use two or more of these four electrodes with at least one configured as an anode and one as a cathode.

Such steps of controlling the direction and shape of the electrical signal applied to the target nerve can be performed after implantation of the microstimulator.

Microstimulators as disclosed herein can be part of a system including a remote pulse generator (not shown) that is in electrical communication with an electrode of the microstimulator and is configured to produce one or more electrical signals. Alternatively, microstimulators can comprise an integral pulse generator. In addition, microstimulators can include an integral battery that is rechargeable by inductive coupling or can be part of a system that includes a remote battery operably coupled to the microstimulator. In other words, a microstimulator may be powered by bringing a power source external to the mammal's body into contact with the mammal's skin or may include an integral power source. As such, a pulse generator or battery may be positioned in any suitable location, such as adjacent to the microstimulator (e.g., implanted adjacent to the microstimulator), integral with the microstimulator, or at a remote site in or on the patient's body.

In some instances, the microstimulator can include its own power source, e.g., which is capable of obtaining sufficient power for operation from surrounding tissues in the mammal's body. Internal power sources can obtain sufficient energy, for example, from muscle movements and other source of body energy generation that can be harnessed via a capacitor or a balloon device that harnesses the energy, for example, so that an internal battery is not needed.

Microstimulators can be pre-programmed with desired stimulation parameters. Stimulation parameters can be controllable so that an electrical signal may be remotely modulated to desired settings without removal of the microstimulator from the target implant site. Remote control may be performed, e.g., using conventional telemetry with an implanted pulse generator and battery, an implanted radiofrequency receiver coupled to an external transmitter, and the like. In some instances, some or all parameters of the microstimulator may be controllable by the subject, e.g., without supervision by a physician. In other instances, some or all parameters of the microstimulator may be automatically controllable by a programmer or controller. A controller can be embodied as software on a multi-purpose external device, such as, for example, a PC, a cell phone, a PDA type device, or tablet.

Certain embodiments as disclosed herein include closed-loop systems. For example, a wearable ankle strap or a physician programmer can have a plug-in sensor to sense EMG activity, sense ENG activity, or measure trigeminal somatosensory evoked potentials (TSEPs), evoked muscle action potentials (EMAPs) or electrically evoked compound action potentials (ECAPs) to determine the minimal threshold of stimulation needed to achieve a therapeutic effect. Identifying the minimal threshold needed for stimulation avoids or minimizes pain for the patient. Such a feature could also be used for troubleshooting, programming, patient feedback etc. Other art stimulates at the highest tolerable level, since they are open loop, with the understanding that such stimulation will result in the highest probability of being efficacious. Also, other art relies on physiological responses such as toe twitches or painful muscle contraction to evaluate the programming settings.

Because a microstimulator according to certain embodiments of the present disclosure is implanted at a site that is above deep fascia, the microstimulator is further away from the target nerve. As such, the variability of distance from such an implant site to the target nerve can be much greater compared to SNS and PTNS both from patient to patient and within a given patient given fluctuations in weight or fluid retention. Such variable distance to the target nerve can undesirably increase the requisite size of a microstimulator. To address such a concern, microstimulators as disclosed herein can have a flat or cylindrical, elongated, low profile configuration. The majority of the microstimulator can be fabricated from or coated with a material so that the microstimulator is "body compliant" and has mechanical properties similar to the tissue at the target implant site. Exemplary materials include polymeric materials with elastic properties or thermal plastics comprising urethane, aromatic polyurethane, silicones, polyethers, polycarbonates, polytetrafluoroethylene, elastane, or combinations thereof.

Figure 6:
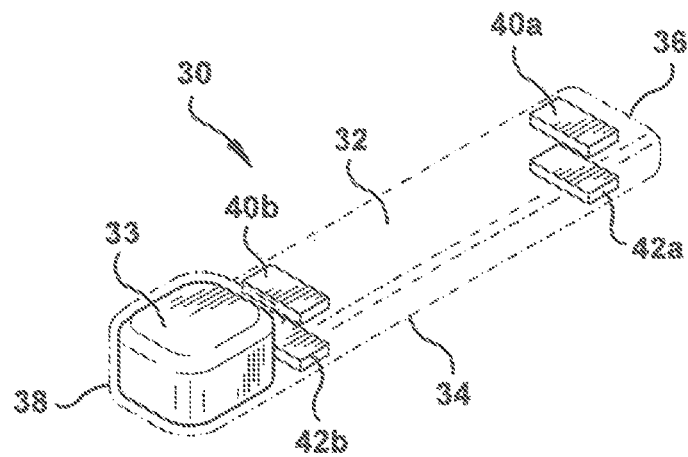
FIG. 6 is a perspective view of a microstimulator according to an embodiment of the present disclosure.

Referring to FIG. 6, in an embodiment, a microstimulator 30 comprises a microstimulator body 31 having a top surface 32, a bottom surface 34, a proximal end 36 and a distal end 38. Microstimulator body 31 can include an enclosure 33 comprising electrical circuitry that is in electrical communication with at least one independently programmable electrode 40 on top surface 32 and/or at least one independently programmable electrode 42 on bottom surface 34. Although FIG. 6 illustrates the enclosure at the distal end of the microstimulator body, the enclosure can be located at the proximal end or anywhere between the proximal and distal end. Further, although electrodes 40 and 42 are illustrated as being spaced from enclosure 33, electrodes 40 and 42 can be disposed on enclosure 33 or other electrodes can be disposed on enclosure 33. The electrical circuitry within enclosure 33 can include microprocessors under the control of a suitable software program. The electrical circuitry can include other components such as an analog-to-digital converter, etc.

In certain embodiments, as depicted in FIG. 6, microstimulator body 31 comprises two independently programmable electrodes 40a and 40b on top surface 32 that are separated by a distance of at least three millimeters and two independently programmable electrodes 42a and 42b on bottom surface 34 that are similarly separated by a distance of at least three millimeters.

As stated above, a micro stimulator can include one or more re-deployable fixation members to securely anchor the microstimulator at the target implant site, which, in certain embodiment, is randomly distributed connective tissue that is above deep fascia and below the skin. Passive anchors such as silicone tines that rely on the springiness of the silicone material to find open space amongst the tissue may not sufficiently fixate a microstimulator to such randomly distributed connective tissue. Re-deployable fixation members as described herein can sufficiently fixate the microstimulator to connective tissue and also can allow the microstimulator to release the connective tissue if necessary so that the microstimulator can be re-anchored. In other words, if the microstimulator does not stimulate the target nerve, the re-deployable fixation members can be withdrawn proximally and released from tissue, the microstimulator can be re-located, and the fixation members can be re-deployed distally and/or laterally.

Figure 8:
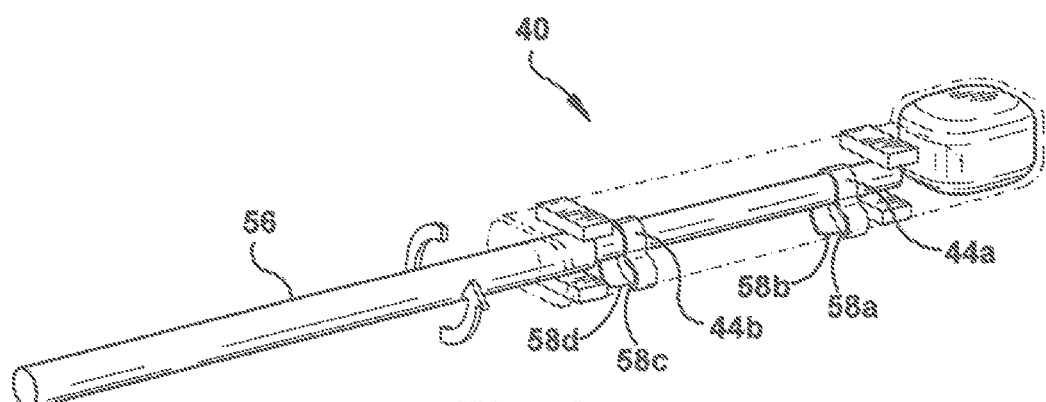
FIG. 8 is a perspective view of the microstimulator of FIG. 7 with the fixation members in a deployed position according to an embodiment of the present disclosure.
Figure 9:
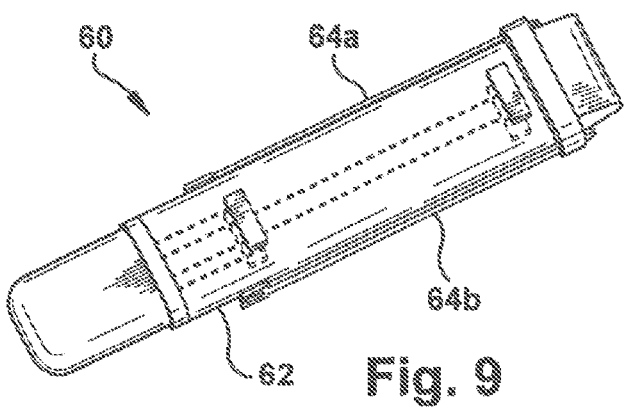
FIG. 9 is a perspective view of a microstimulator with fixation members in a non-deployed position according to an embodiment of the present disclosure.

Such re-deployable fixation members can be disposed on the top, bottom or lateral surfaces of the microstimulator body and there can be a single or multiple re-deployable fixation members disposed on the microstimulator body. In a preferred embodiment, re-deployable fixation members are disposed on the lateral sides of the microstimulator body as illustrated in FIGS. 8 and 9 described in more detail below. Such a configuration can ensure that the electrodes of the microstimulator are correctly oriented towards the target nerve and that the fixation members are urged outward (lateral deployment) in a plane that is substantially parallel to the field of deep fascia. Also the re-deployable fixation members can include tissue interfacing components such as, for example, tines, barbs, teeth, or pincers to provide redundant fixation to ensure successful positioning and anchoring in connective tissue of the anatomical region. In embodiments, where the fixation members are anchored to tissue above deep fascia and below the skin, the fixation members can be fabricated and configured to lack certain mechanical properties (e.g. shape, tensile strength, cross-section, aspect ratio, etc.) necessary to pierce deep fascia.

Figure 7:
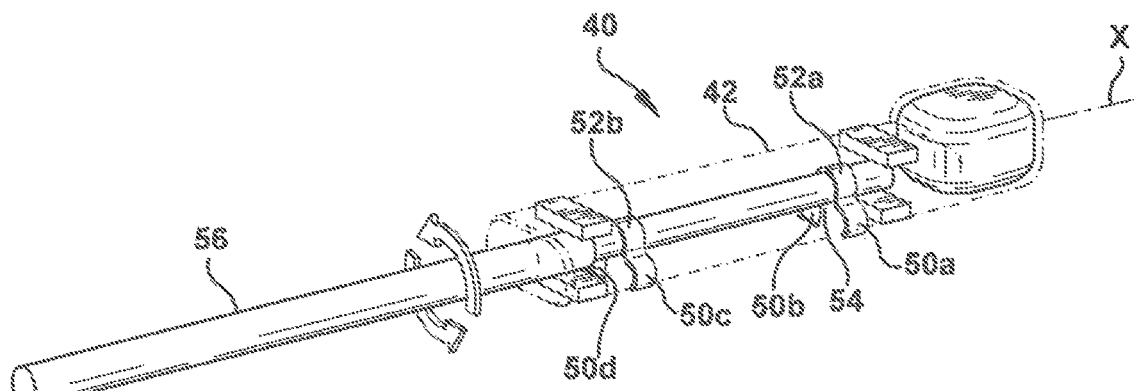
FIG. 7 is a perspective view of a microstimulator with fixation members in a non-deployed position according to an embodiment of the present disclosure.

Referring to FIGS. 7 and 8, in an embodiment, microstimulator 40 comprises stimulator body 42 having re-deployable fixation member 44 attached thereto. Although FIG. 7 depicts two fixation members 44A and 44B, the microstimulator can include a single fixation member or more than two fixation members. Each fixation member 44 can be a clip including two flexible arms 50 separated by clip base 52 that defines receiving space 54. Although arms 50 of fixation member 44 are illustrated as being disposed substantially perpendicular to the longitudinal axis X of microstimulator body 42, the fixation member can be attached to the microstimulator body such that the arms extend in a plane substantially perpendicular to the longitudinal axis X of the microstimulator body.

As illustrated in FIG. 7, delivery tool 56 can be inserted into receiving space 54 of fixation member 44 to engage clip base 52. Once reaching an anatomical site, delivery tool 56 can be rotated to splay open arms 50. Referring to FIG. 8, to anchor microstimulator 40 into the connective tissue at the implant site, delivery tool 56 can be rotated in the opposite direction to urge the tips 58 of arms 50 together thereby grabbing and pinching the surrounding connective tissue and affixing microstimulator to the target implant site. If microstimulator 40 needs to be re-anchored, delivery tool 56 can be rotated back again to splay open arms 50 to release the connective tissue and fixation member 44 can be redeployed at a different implant site. The microstimulator can be anchored to an implant site substantially parallel to the target nerve or substantially perpendicular to the target nerve. In embodiments where the microstimulator is fabricated from a body compliant material, the microstimulator can be compressed in an upward or outward direction when the delivery tool is rotated providing additional closing pressure on the fixation member. The tips of the arms of the fixation member can comprise one or more tines for grabbing and pinching connective tissue and the angle between multiple tines can range from between about 0 to about 90 degrees. Having multiple locations where the microstimulator is fixated to surrounding connective tissue via multiple fixation members or multiple tines at a tip of the fixation member increases the surface area of the microstimulator that is in contact with the connective tissue and provides strain relief from forces acting to dislodge the microstimulator.

Figure 10:
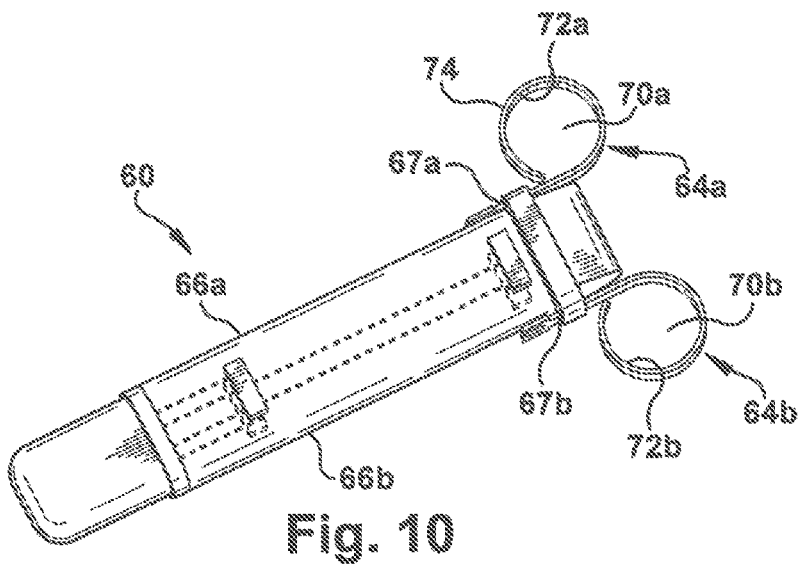
FIG. 10 is a perspective view of the microstimulator of FIG. 9 with the fixation members in a deployed position according to an embodiment of the present disclosure.

Referring to FIGS. 9 and 10, in another embodiment, microstimulator 60 comprises a microstimulator body 62 having side 66 and re-deployable fixation member 64 slidably attached to side 66. FIG. 9 depicts microstimulator 60 having first side 66a and second side 66b and two fixation members 64A and 64B attached respectively to first and second sides 66a and 66b of microstimulator body 62. However, the microstimulator can include a single fixation member or more than two fixation members. In this embodiment, fixation member 64 assumes a coiled configuration in a deployed state, as illustrated in FIG. 10, and a substantially linear configuration in a non-deployed state, as illustrated in FIG. 9. The fixation members can be fabricated from a material that allows such a change in configuration. For example, the fixation member can be fabricated from a super-elastic material, polymeric materials, silicone based materials or combinations thereof. The outer surface of the fixation member can include jagged barbed edges 74 as illustrated in FIG. 10 to increase the holding force of the fixation member. Additionally, the body of the fixation member can include features, such as holes, which allow tissue ingress to increase the holding force of the fixation member.

A delivery tool can releasably engage the fixation member to urge the fixation member distally or to retract the fixation member proximally. For example, fixation members 64A and 64B can include apertures that are sized and configured to receive a projection disposed on the delivery tool in order to releasably couple the delivery tool to the fixation member. When loaded into a delivery tool, fixation members 64A and 64B assume a substantially linear configuration against respective sides 66a and 66b of microstimulator body 62 as illustrated in FIG. 9. When reaching the anatomical site, the delivery tool can urge the fixation members 64A and 64B distally through slots 67a and 67b, for example, defined by respective first and second side 66a and 66b of microstimulator body 62. Fixation members 64A and 64B return to their original coiled shape as illustrated in FIG. 10 capturing connective tissue within the space 70 defined by the interior surface 72 of the coiled portion of the fixation members 64A and 64B. The interior diameter of the coiled portion of the fixation member can be increased or decreased to optimize captured tissue volume. If microstimulator 60 needs to be re-anchored, the delivery tool can retract fixation members 64A and 64B back through slots 67a and 67b to release the connective tissue and fixation member 64 can be re-deployed into connective tissue at a different location.

Although the above embodiments describe re-deployable fixation members, other types of fixation members can be used such as deployable, passive or dissolvable fixation members. In an embodiment, a fixation member can comprise a reservoir for a deployable biocompatible liquid polymer. Such a reservoir can be located on the delivery tool or the microstimulator itself and can contain the biocompatible polymer in a liquid phase. Such a polymer can have tissue adherent properties that facilitate fixation of the microstimulator to surrounding connective tissue. Further, such a liquid polymer can have properties such that when deployed from its reservoir it is in the liquid phase, for example, and as time progresses after deployment, it can increase fixation of the microstimulator to adjacent tissue by forming a semi-solid or solid membrane between the microstimulator and surrounding connective tissue.

Figure 11:
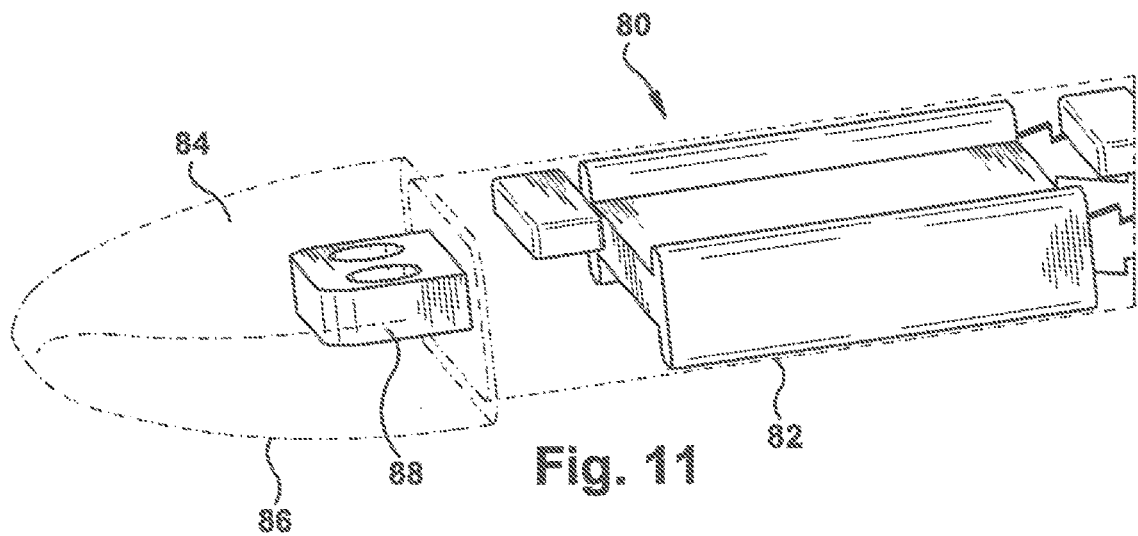
FIG. 11 is a perspective view of the distal end of a microstimulator according to an embodiment of the present disclosure.
Figures 12, 13:
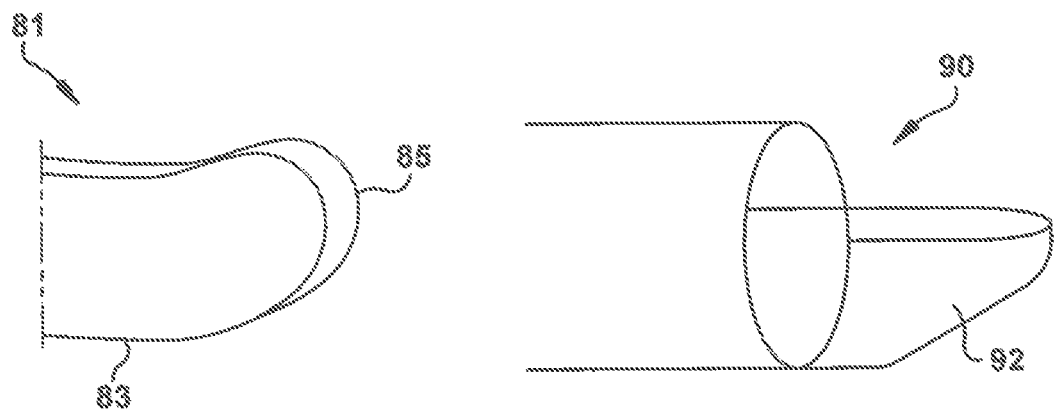
FIG. 12 is a perspective view of the distal end of a microstimulator according to an embodiment of the present disclosure.
FIG. 13 is a perspective view of the distal end of a delivery tool according to an embodiment of the present disclosure.

In embodiments where microstimulator is implanted above deep fascia, microstimulators can include features to facilitate tunneling through skin to an implant site without penetrating deep fascia. For example, the distal end of the microstimulator can be blunt, round, wedge-shaped, asymmetrical, or trowel shaped. Further, the distal end of the microstimulator can be fabricated from an elastomeric material, such as silicone for example, so that the tip does not pierce deep fascia and conforms to the space within tissue of the anatomical region. Referring to FIG. 11, in an embodiment, microstimulator 80 comprises microstimulator body 82 having a wedge-shaped distal tip 84. Such a tip configuration prevents the microstimulator from puncturing deep fascia and also helps guide the microstimulator to the implant site. The distal tip can comprise rigid structure 86 encased by elastomeric overmold 88. Non-limiting examples of elastomeric materials include silicone and thermoplastic polyurethane. In other embodiments, the distal end is blunt but does not have an elastomeric casing. Referring to FIG. 12, in other embodiments, microstimulator 81 comprises a microstimulator body 83 having an asymmetrical, "toboggan-shaped" distal tip 85. In such an embodiment, the distal most point of the tip can be off center from the longitudinal axis of the microstimulator.

A delivery tool used to implant a microstimulator can also include features to facilitate tunneling through skin to an implant site without penetrating deep fascia and to also evaluate whether the microstimulator is sufficiently anchored to the implant site thereby indicating that the fixation member is sufficiently anchored to connective tissue of the anatomical region. Referring to FIG. 13, a delivery tool 90 can have a deflectable "ski like" tip 92 that provides for blunt dissection of subdermal tissue prior to reaching deep fascia to avoid penetration of deep fascia. With respect to evaluating anchoring strength, tip 92 can deflect only when a certain amount of axial force has been reached. For example, tip 92 can have a forward deflection force calibrated to the desired anchoring holding force of a fixation member of a microstimulator.

Figure 14:
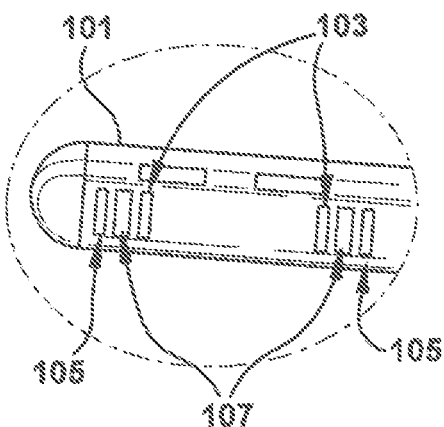
FIG. 14 is a bottom view of a delivery tool and a microstimulator inserted therein according to an embodiment of the present disclosure.

Microstimulators and delivery tools can also include features that allow a clinician to detect deep fascia as the microstimulator is inserted into tissue in embodiments where the implant site is above deep fascia and below the skin. Such features include mechanical or electrical sensors. For example, referring to FIG. 14, a delivery tool 101 can include sensing electrodes 103 and stimulation electrodes 105 to provide for real-time monitoring of impedance between the electrode pairs. The stimulation electrodes 105 of the microstimulator 107 can also be used as stimulation sources for impedance measurements by exposing tissue outside delivery tool 101. Impedance generally decreases from the skin to deep fascia. As such, typical fascia tissue has lower impedance than tissue above deep fascia. Therefore, a clinician can detect when the electrodes are in contact with fascia. In other words, while the delivery tool is advanced along the tissue to an implant site, impedance can be monitored to provide feedback so that the delivery tool maintains contact with the tissue along the surgical pathway but does not penetrate into deep fascia. Such feedback can be provided to the clinician during insertion to detect the deep fascia, to ensure that the delivery tool reaches the interface between tissue above deep fascia and the deep fascia layer, and allow for a change of insertion angle to prevent puncture of deep fascia. Further, during advancement of the delivery tool and microstimulator, real time monitoring is possible to ensure continued contact with tissue above the deep fascia. Impedance monitoring electrodes can also be used for stimulation and/or sensing during implant procedures for locating or detecting the target nerve or for target nerve capture confirmation testing to determine the target implant site.

Figure 15:
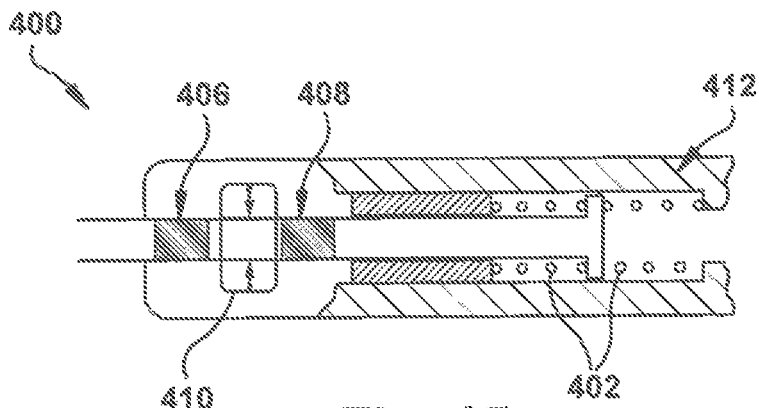
FIG. 15 is a partial cross-sectional view of a delivery tool according to an embodiment of the present disclosure.

Microstimulators and delivery tools can also include features that allow a clinician to both detect deep fascia as the microstimulator is inserted into connective tissue as well as determine whether the microstimulator is sufficiently anchored in the connective tissue site. For example, with reference to FIG. 15, a delivery tool 400 can include a two spring system with one spring system for sensing fascia and the other spring system for verifying anchoring force. Regarding sensing fascia, when the microstimulator (not shown) is inserted and touches the stiffer layer of deep fascia it faces higher resistance and the reaction force will overrun the stiffness of spring 402 and compresses spring 402. As a result, fascia indicator 406 will appear in indicator window 410. Regarding anchoring force, after deployment of a fixation member of the microstimulator, a pull on handle 412 will apply a tag force on the distal end of the microstimulator. If the anchoring force is adequate, anchoring indicator 408 will stay in place while indicator window 410 moves proximally with handle 412. Anchoring indicator 408 will be viewed through indicator window 410. If the anchoring force is not adequate, such force will not be able to keep anchoring indicator 408 in place thus anchoring indicator 308 will move with handle 412 as well and thus will not appear in indicator window 410. Other methods of confirming anchoring integrity include the use of a Hall sensor with a spring.

As described above, a delivery tool can include stimulation and/or sensing electrodes to provide an electrical signal during the implant procedure, while monitoring for sensed nerve activation, such as EMG or ENG signals, for example. Nerve activation can be monitored in other ways as well. The stimulation or sensing electrodes can be on multiple sides of the delivery tool to allow for stimulation and nerve capture sensing of more than one nerve. By exposing electrodes on the microstimulator to the external tissue, the microstimulator electrodes can also be used for stimulation or sensing. Further, one electrode of an array of electrodes on the microstimulator or delivery tool can be used to provide a stimulation signal while the other electrodes can be used to sense resulting nerve activation signals such as EMG or ENG signals, for example. In addition, sensing can be done from external electrodes placed on the skin, such as EMG or ENG electrodes. The delivery tool can include visual feedback indications relating to target nerve activation such as LED indicators Such localization features that are utilized while the delivery tool is advanced provide feedback for target microstimulator placement adjacent a target nerve. Further, multiple feedback signals can be obtained if targeting more than one nerve.

Regarding determining a target implant site such that the target nerve is localized and the target nerve is captured, as an example, stimulation electrodes of a delivery tool or a microstimulator can deliver an electrical stimulation signal of a certain waveform. Example stimulation waveforms are shown in FIG. 16, and include a single pulse (shown in example A), a bipulse (shown in example B), an alternating bipulse (shown in example C), a sweep (shown in example D), a burst (shown in example E), or the like. A pulse in each waveform can be followed by a predetermined duration during which charge is recaptured from the anatomical site. This charge recapture can be achieved in a passive mode or an active mode for example, by reversing the polarity of the stimulating electrodes for a predetermined duration. Application of the electrical signal can be followed by a detection window of a pre-defined time. The detection window can occur concurrently with the charge recapture. During the detection window, sensing electrode of the delivery tool, microstimulator, or on the surface of the patient's skin, can detect an EMG due to a muscle contraction. When the electrical signal stimulates the target nerve (including the tibial nerve or saphenous nerve, for example), the muscle will contract and an EMG signal will be generated. Example localization methods for each type of waveform are shown in FIGS. 17-21.

Figure 23:
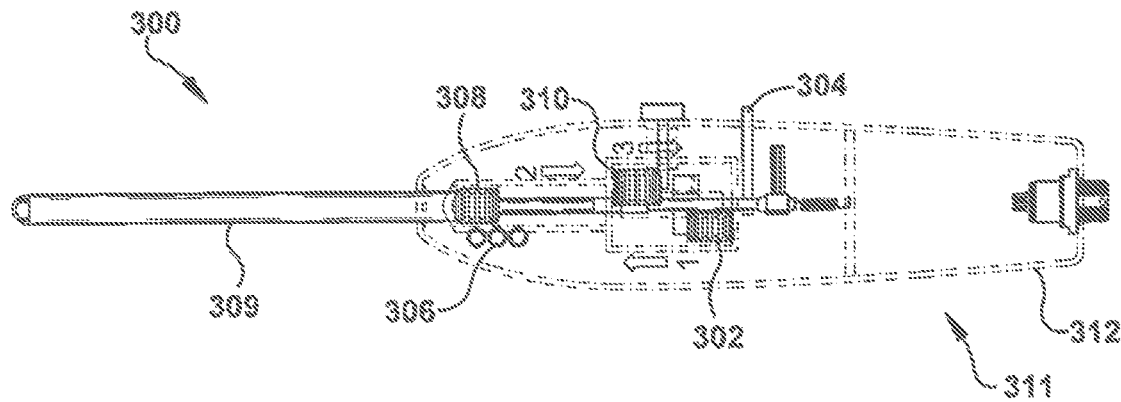
FIGS. 23-30 are schematic illustrations of an insertion tool and depict various stages of deployment of a microstimulator according to an embodiment of the present disclosure.

A target implant site can be determined, for example, using the system of FIG. 23. An example microstimulator is shown in the block labeled MICROSTIMULATOR. The sensing electrodes are labeled SENSOR(S). The block labeled OUTPUT can provide tactile feedback, visual feedback, and/or audio feedback of the proximity of the MICROSTIMULATOR to the target nerve (in other words, whether the target nerve is captured). The OUTPUT can provide any other kind of feedback, including mechanical feedback in the form of pressure or vibratory energy transmitted to the operator by an appropriate transducer. However, the feedback can be implemented in different/alternative ways.

A stimulation pattern of a predetermined amplitude (Siga) can delivered by the MICROSTIMULATOR. Sensing can be started simultaneously at the SENSOR(S), yielding a measured signal (Sigb). Siga and Sigb can be simultaneously compared to each other statistically and/or mathematically using signal processing techniques to capture relevant information from both signals. When a mathematical cross-correlation of Siga and Sigb yields a significant cross-correlation $C_{a-b}$ such that correlation $C_{a-b}$ exceeds a predetermined value, capture of the target nerve can be determined to have occurred. In some examples, once capture has occurred, the audio speaker can start emitting an audible sound to the operator, and/or the LED can indicate a visual signal to the operator, and/or the mechanical transducer can transmit a mechanical Tactile signal to the operator. The magnitude of the output from speakers, LED, and Tactile can be modulated proportional to the cross-correlation $C_{a-b}$, to indicate increasing or decreasing proximity of the MICROSTIMULATOR to the target nerve.

Figure 16A:
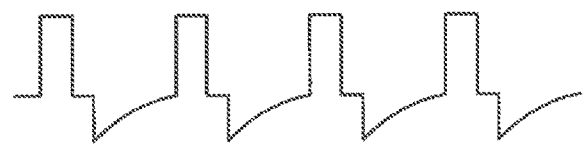
FIGS. 16A-E are sample waveforms that could be used to determine a target implant site to which a microstimulator is anchored.
Figure 17:
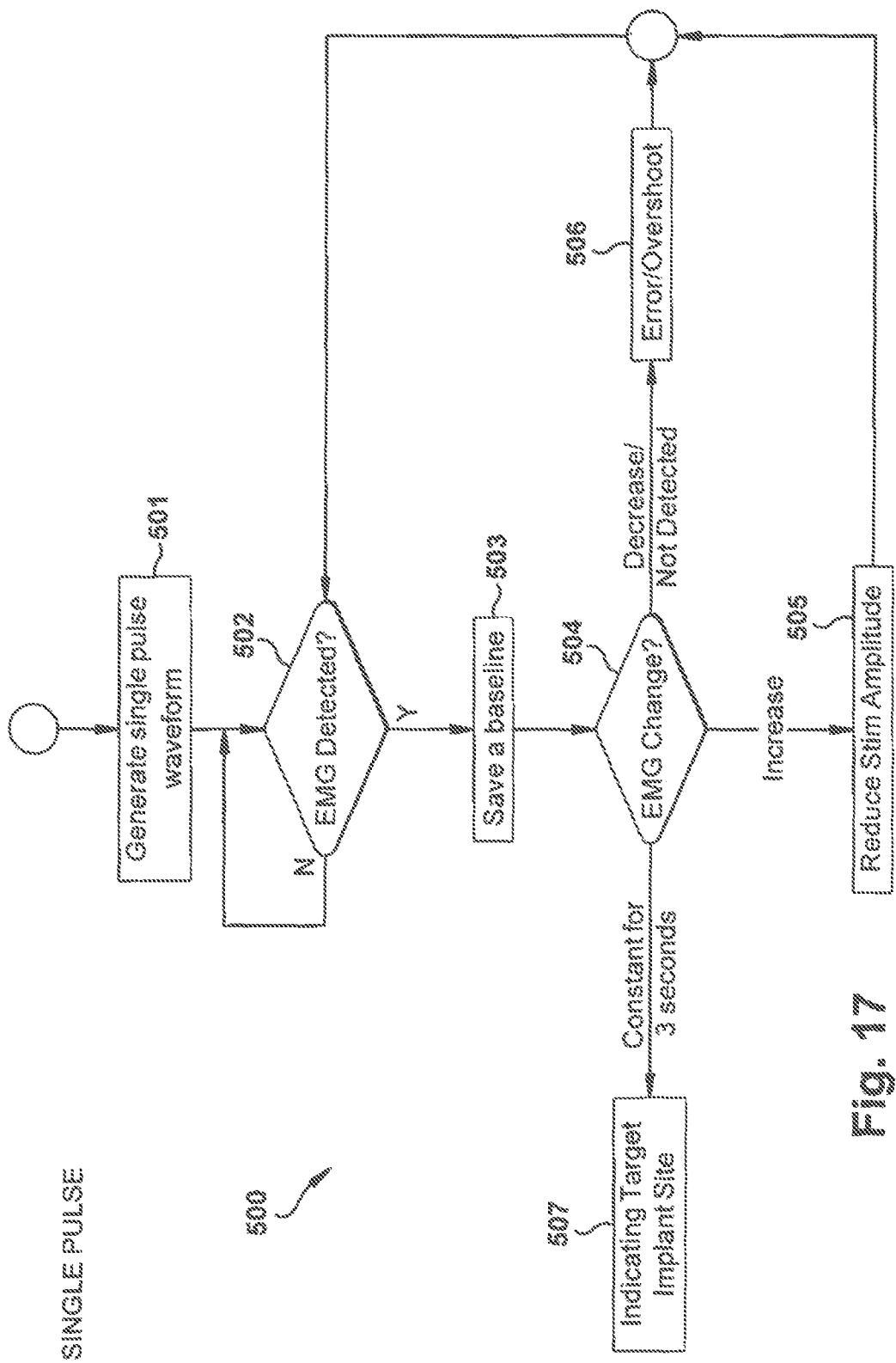
FIGS. 17-21 are flow diagrams indicating steps of a method of determining a target implant site in which to implant a microstimulator according to embodiments of the present disclosure.

Various examples of stimulation waveforms that can be applied by the microstimulator or delivery tool and methods of using these stimulation waveforms to determine a target implant site are described below. As shown in FIG. 16A, a single pulse stimulus waveform can be generated at a given amplitude, pulse width, frequency, and interphase delay and can be delivered by an electrode included with the delivery tool or the microstimulator. A detection window of time can follow after application of each pulse of the single pulse stimulus waveform. During the detection window, sensors can monitor for the EMG signal resulting from the stimulation. Referring to FIG. 17, in an embodiment of a method (500) of determining a target implant site, a single pulse stimulus waveform can be generated (step 501) and can be delivered by an electrode. The first detection of the EMG can be set as the baseline EMG (including, for example, the strength, power, and/or root mean square (RMS) value) (steps 502-503). Thereafter, EMG activity can continue to be detected (step 502), and on re-detection, method (500) can comprise reduction of the amplitude of the single pulse stimulus waveform on increase of the EMG from baseline (step 505). For example, the amplitude can be reduced by 10%. Method (500) then can comprise continued detection for a stimulation evoked EMG (step 502). If an EMG is still elicited by the lower amplitude signal (a decrease is expected based on the reduced stimulation amplitude), this EMG can be stored as a new baseline value (including, for example, the strength, power, and/or RMS value) (step 503). If the EMG is no longer detected or decreases from the baseline, the stimulation can be restored to the previous amplitude, and an error/overshoot condition can be indicated to the user (step 506). However, if the EMG remains constant for a time period (e.g., three seconds or more), the delivery tool can be determined to be at a target implant site (step 507).

Figure 16B:
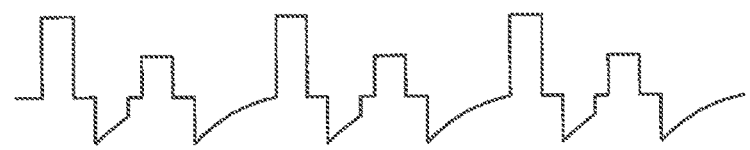
Figure 18:
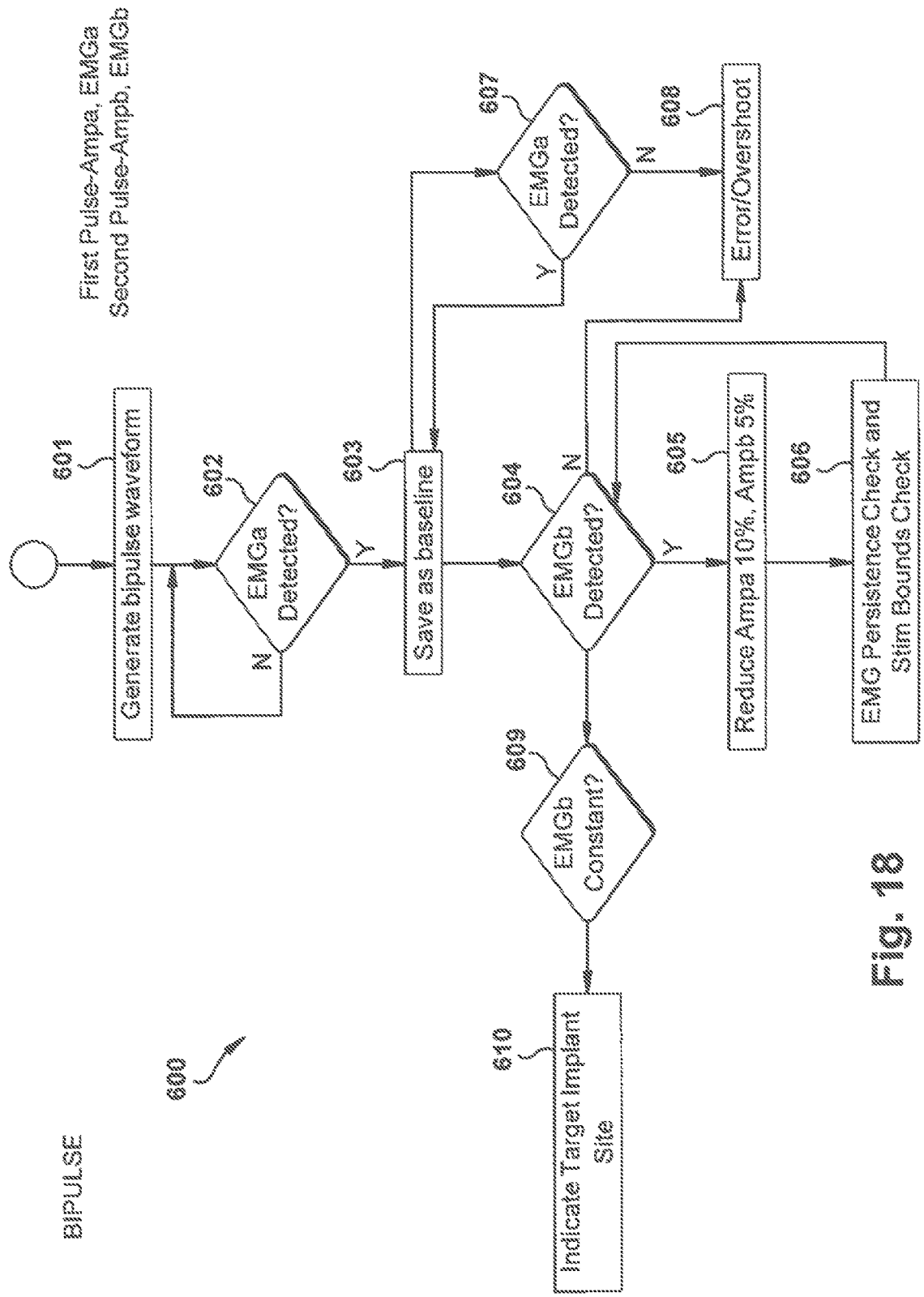

As shown in FIG. 16B, a bipulse stimulus waveform can be generated and can be delivered by an electrode included with the delivery tool 5 or microstimulator 10. Referring to FIG. 18, in an embodiment of a method (600) of determining a target implant site, a bipulse stimulus waveform can be generated (step 601) and can be delivered by an electrode. The bipulse stimulus waveform can be a repetition of a pulse pair. The bipulse stimulation can have a single frequency for the paired pulses. The first pulse in the pair can have a first amplitude (Ampa) and the second pulse in the pair can have a second amplitude (Ampb). The second amplitude can be less than the first amplitude for example by 25%. A detection window of a predetermined duration can follow after application of every pulse (step 602). During the detection period, a first EMG corresponding to the first pulse (EMGa) and a second EMG corresponding to the second pulse (EMGb) can be detected. The first detection of the first EMG (EMGa) can be set as the baseline EMG (including, for example, the strength, power, and/or RMS value) (step 603). Thereafter, method (600) can comprise continuation of detection of a stimulation evoked first EMG (EMGa) (step 607) and initiating detection for a second EMG (EMGb) (step 604). When a second EMG (EMGb) is detected, the amplitude of the first (Ampa) and second pulse (Ampb) can be decreased (step 605). For example, the amplitude of the first pulse can be reduced by 10% for example and the amplitude of the second pulse can be reduced by 5% for example. The sensors can again monitor for resulting EMGs (steps 604 and 607). If a first EMG (EMGa) is still elicited by the lower amplitude signal (a decrease is expected based on the reduced stimulation amplitude), this EMG can be stored as a new baseline value (including, for example, the strength, power, and/or RMS value) (step 603). If EMG due to stimulation (EMGa or EMGb) is no longer detected, the stimulation amplitudes for both pulses can be restored to the previous amplitude, and an error/overshoot can be indicated (step 608). If at any time the amplitude of the first pulse is less than the amplitude of the second pulse in the pulse pair, the amplitude of the first pulse can be set equal to the amplitude of the second pulse (step 606). If the second EMG remains constant for a time period (e.g., three seconds), the delivery tool can be determined to be at a target implant site (steps 609-610).

Figure 16C:
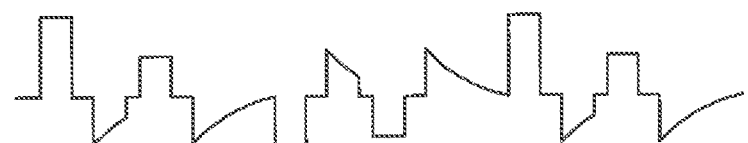
Figure 19:
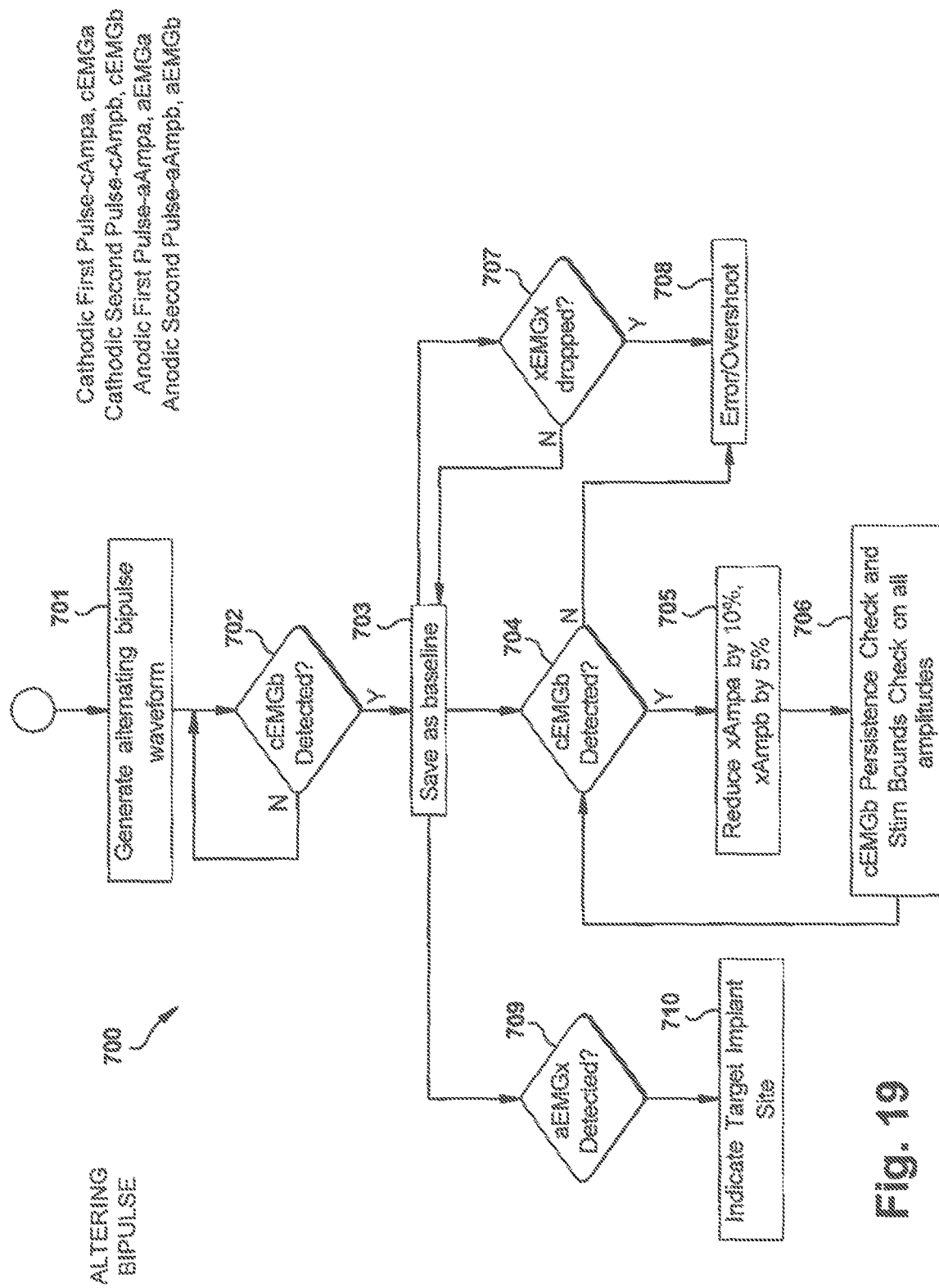

As shown in FIG. 16C, an alternating bipulse stimulus waveform can be generated and can be delivered by an electrode included with the delivery tool or microstimulator. Referring to FIG. 19, in an embodiment of a method (700) of determining a target implant site, an alternating bipulse stimulus waveform can be generated (step 701) and can be delivered by an electrode. The alternating bipulse stimulus waveform can be a repetition of a pulse pair. Every pulse pair can be delivered at a polarity that is opposite to that of the preceding pulse pair. The alternating bipulse stimulation can have a single frequency for the paired pulse. Furthermore, in method (700), each paired pulse can comprise a first pulse with a first amplitude (cathodic: cAmpa, anodic: aAmpa) and, a second pulse with a second amplitude (cathodic: cAmpb, anodic: aAmpb). The second pulse amplitude in a pulse pair, can be less than the first amplitude for example by 25%. The electrical polarity of every pair of pulses can be reversed. For example, the pulses can be paired so that the first amplitude and the second amplitude are both cathodic, and then the next pair of the first amplitude and the second amplitude are both anodic to achieve an inversion.

A detection window of a predetermined duration can follow after application of each pulse of an alternating bipulse stimulus waveform. During the detection period, a first cathodic EMG corresponding to the first cathodic pulse (cEMGa), a second cathodic EMG corresponding to the second cathodic pulse (cEMGb), a first anodic EMG corresponding to the first anodic pulse (aEMGa), and a second anodic EMG corresponding to the second anodic pulse (aEMGb) can be detected. The first detection of the second cathodic EMG (cEMGb) can be set as the baseline EMG (including, for example, the strength, power, and/or RMS value) (step 702-703). Subsequently, after the initial determination of the baseline, method (700) can comprise continued monitoring of second cathodic stimulation pulsed evoked muscle EMG (cEMGb), (step 704). On continued detection second cathodic EMG (cEMGb), (step 704), the subsequent pulses in the alternating bipulse waveform can be generated with a reduced amplitude (step 705). For example, the amplitude of the first anodic and cathodic pulses (cAmpa, aAmpa) can be reduced by 10%, and the amplitude of the second anodic and cathodic pulses (cAmpb, aAmpb) can be reduced by 5%. The sensors can again monitor for resulting EMGs, (step 704). If a second EMG is still elicited by the lower amplitude signal (a decrease is expected based on the reduced stimulation amplitude), this EMG can be stored as a new baseline value (including, for example, the strength, power, and/or RMS value), (steps 703 and 707). Method (700) can further comprise, if an already detected EMG is no longer detected or decreases from the baseline, restoring stimulation to the previous amplitude, and an error/overshoot condition can be indicated, (steps 704, 707, and 708). At any time, if the amplitude of the first EMG, (cAmpa, aAmpa) is less than the amplitude of the second EMG, (cAmpb, aAmpb), the amplitude of the first pulse can be set equal to the amplitude of the second pulse, (step 706). If EMG activity is detected on any anodic stimulus pulse, (aEMGa or aEMGb), the delivery tool can be determined to be a target implant site (step 709 and 710).

Figure 16D:
Figure 20:
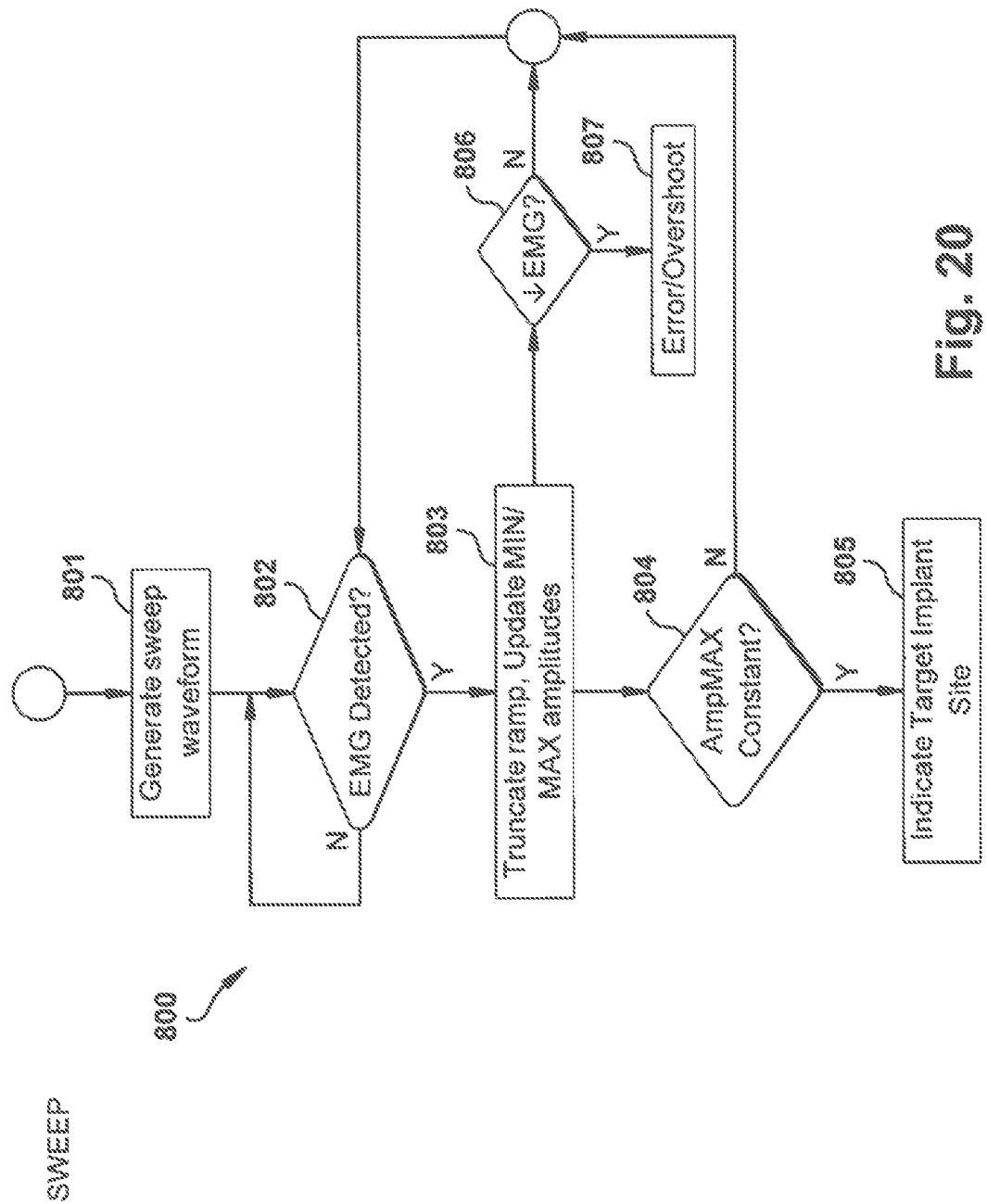

As shown in FIG. 16D, a sweep stimulus waveform can be generated and can be delivered by an electrode included with the delivery tool or microstimulator. Referring to FIG. 20, in an embodiment of a method (800) of determining a target implant site, a sweep stimulus waveform can be generated (step 801) and can be delivered by an electrode. A sweep stimulus waveform can be, for example, a train of pulses generated at a pre-determined frequency and an increasing amplitude. Each pulse can be followed by a detection window. The train of pulses can be repeated after a maximum amplitude is reached. There may or may not be a pause in between the repetition of the pulse train. This implies two frequencies—one frequency for the pulse in the pulse train and another for the repetition of the pulse train.

In method (800), when a search algorithm is initiated, for example, a train of cathodic pulses can be generated. The first pulse can start at a sub-threshold value (e.g., 1 mA) and each subsequent pulse in the train can increase by a predetermined amplitude, such as 500 µA for example, until a maximum amplitude (e.g., 20 mA) is reached. Each pulse can be followed by a respective detection window. Method (800) can comprise detection of EMG due to nerve stimulation (steps 802 and 803) such that, if such EMG is detected in any detection window, the remaining pulses in the train can be terminated, the amplitude of the pulse that elicited an EMG can be saved as the maximum amplitude, the minimum amplitude can be set to half of the maximum amplitude for example, and the waveform can be restarted. If the pulse amplitude reaches a maximum amplitude (20 mA for example), with no detection of an EMG, the train can be reset and restart at the minimum amplitude. If an EMG has been detected and the maximum amplitude remains constant on three consecutive pulse trains, a target implant site can be indicated to the operator, (steps 804-805). If an EMG has been detected on a previous train of pulses, and the maximum amplitude is reached without detecting the EMG, the maximum amplitude can be increased by 500 µA for example unless the maximum amplitude is 20 mA for example. If the maximum amplitude is 20 mA for example and a detected EMG is not re-detected on three subsequent pulse trains, an Error can be indicated (steps 806-807). If the maximum amplitude is increased twice consecutively after having detected an EMG due to nerve stimulation, an Overshoot can be indicated (steps 806-807).

Figure 16E:
Figure 21:
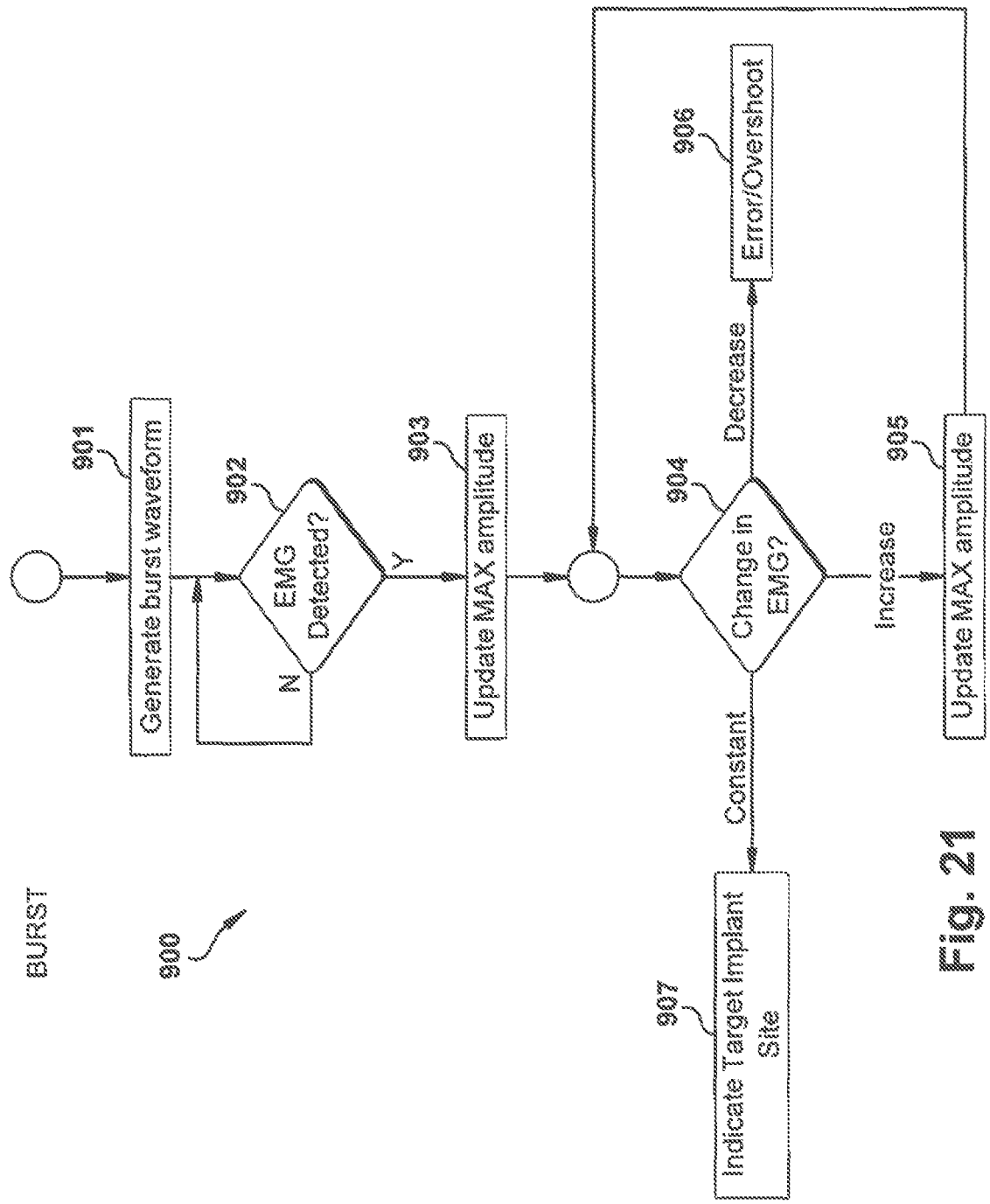
Figure 22:
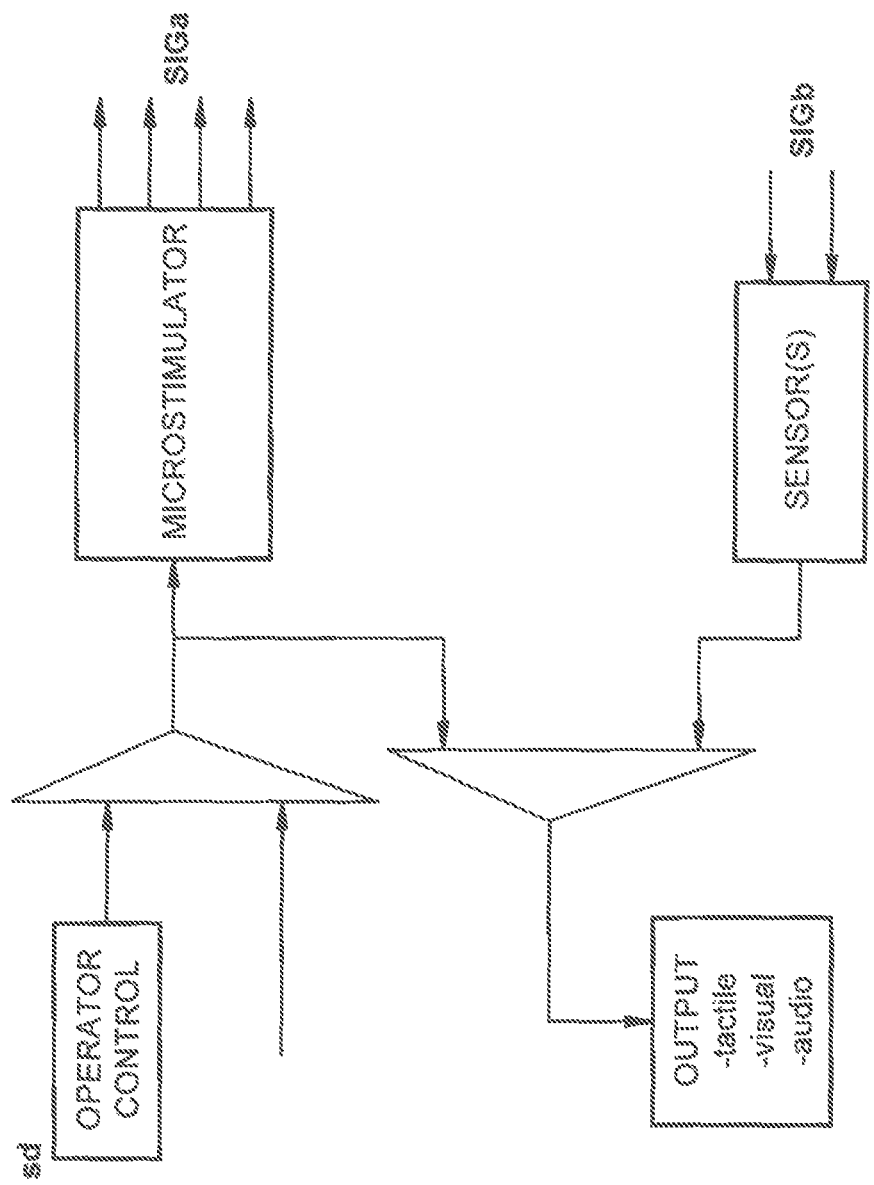
FIG. 22 is a block diagram of components of a system used to determine a target implant site to which a microstimulator is anchored.

As shown in FIG. 16E, a burst stimulus waveform can be generated and can be delivered by an electrode included with the delivery tool or microstimulator. Referring to FIG. 21, in an embodiment of a method (900) of determining a target implant site, a burst stimulus waveform can be generated (step 901) and delivered by an electrode. A burst stimulus waveform can be, for example, five cathodic or anodic pulses at the same polarity for a predetermined frequency (e.g., 20 Hz). The pulse burst can be repeated at another frequency (e.g., 2 Hz). As a result, each burst lasts for a time period (e.g., 250 ms) with a delay (e.g., 250 ms) between the last pulse of one burst and the first pulse of the next burst. The pulses can start at an amplitude (20 mA for example) and each burst can have an overlapping EMG detection window that can extend before the start and beyond the end of each burst, for example 100 ms before and 100 ms after a burst. The burst frequency and the amplitude can be chosen to induce tetanic contraction of the muscle (approximating a 100 ms twitch with a 70 ms relaxation phase, an interpulse delay of 50 ms between the suprathreshold pulses should summate to tetany, for example). Since tetanic, or near tetanic, contraction is expected, the average EMG signal can be compared to the baseline EMG to detect for tetanic recruitment. Expanding the EMG detection before the start of the burst can allow the baseline EMG to be noted and a stimulation EMG to be distinguished from an underlying EMG tone.

Method (900) further comprises continuous detection of EMG due to nerve stimulation, (step 902). When an EMG due to tetanic stimulation is detected, or an increase in EMG signal is detected, the amplitude of the pulses can be decreased by 10% for example and the EMG level noted, (steps 903 and 905). If the EMG due to nerve stimulation remains constant on multiple consecutive bursts, for example four or more consecutive bursts, a target implant site can be indicated to the operator, (steps 904 and 907). If the EMG due to nerve stimulation decreases on multiple consecutive bursts, for example two or more consecutive bursts, an Error and/or Overshoot can be indicated to the operator, (steps 904 and 906).

FIGS. 23-30 are schematic illustrations of an insertion tool 300 and depict various stages of deployment of an embodiment of a microstimulator 400. Insertion tool 300 includes a handle 311 comprising a handle body 312. Extending from handle body 312 is a sheath 309 having a tip for fascia detection and/or protection 301. Such a tip can include any of the features described above for detecting deep fascia and avoiding puncturing deep fascia. Handle body 312 also includes a slider for anchor deployment 302, an anchor sensor lock 304, an anchor feedback sensor 306, a slider 308 for sheath 309, a slider for microstimulator release 310, and a microstimulator release lock 312. Optical guidance systems or technology, such as Optical Spectroscopy, Optical Coherence Tomography or Optical Fiber Probes, can also be used to identify when the delivery tool has reached the deep fascia in embodiments where the implant site is above deep fascia. As part of a system, one or more biocompatible, mechanically robust, optical fibers with less than approximately one mm cross-section, high aspect ratios in excess of 100:1 can be effectively integrated with the delivery tool. Optical spectroscopy techniques exploit the fact that different biological tissue types are characterized by different absorption/reflection spectra, depending on their physical composition. In other words, skin, fascia, fat, muscle, and ligaments include different types, sizes, shapes and orientation of cells, providing distinctly different optical properties, e.g. refractive index and absorption coefficients, which can be used for tissue identification at the tip of the delivery tool and closed-loop guidance of the tip to the deep fascia. Similarly, Optical Coherence Tomography is another embodiment of an optical guidance technique that can be used to detect if the delivery tool has reached the deep fascia. The Fourier domain of this technique uses optical fibers and low coherence interferometry to produce two-dimensional images of a few micrometers in axial resolutions at a high rate, enabling real-time feedback to the physician during the procedure. Another embodiment can utilize a fiber Bragg grating, a type of distributed Bragg reflector, constructed in a short segment of one or more optical fibers that reflects particular wavelengths of light and transmits all others. The fiber Bragg grating strain sensor can act as a pressure gauge that discriminates between different types of tissue along the (tunnel to the implant site) thus providing continuous and real time measurements of the pressure experienced by the delivery tool tip during its advancement. The deep fascia can be localized by detecting the abrupt deflection of the fiber and resulting Bragg wavelength shift due to the passage from a soft adipose tissue region to the thing and strong "hard" deep fascia tissue. During the procedure, a delivery tool system can monitor the Bragg wavelength shift as a function of time in response to the different degree of elasticity and consistency of the tissue being penetrated thereby making it possible to distinguish the tissue boundary at the deep fascia from the other boundaries.

Figure 24:
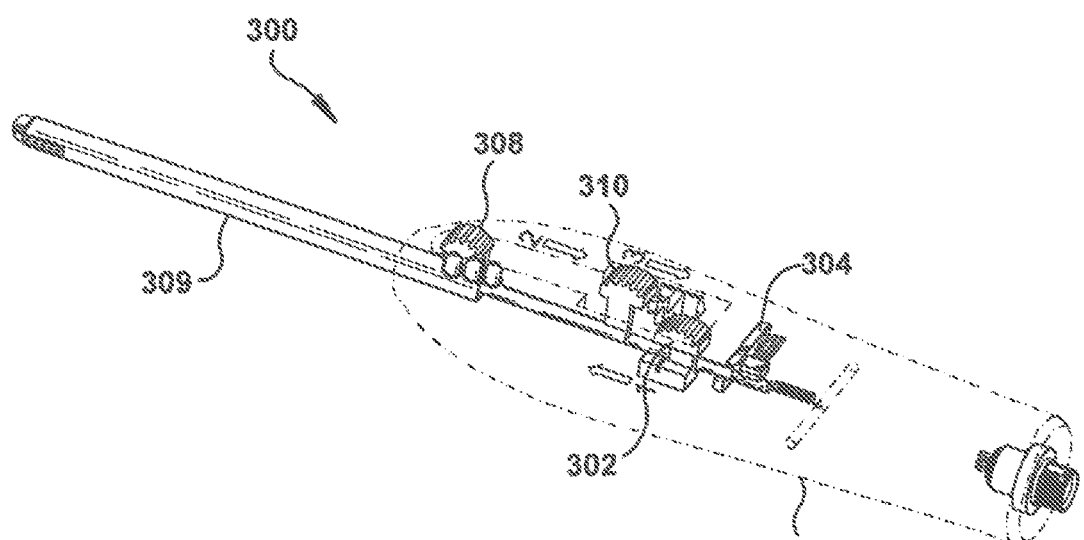
Figure 25:
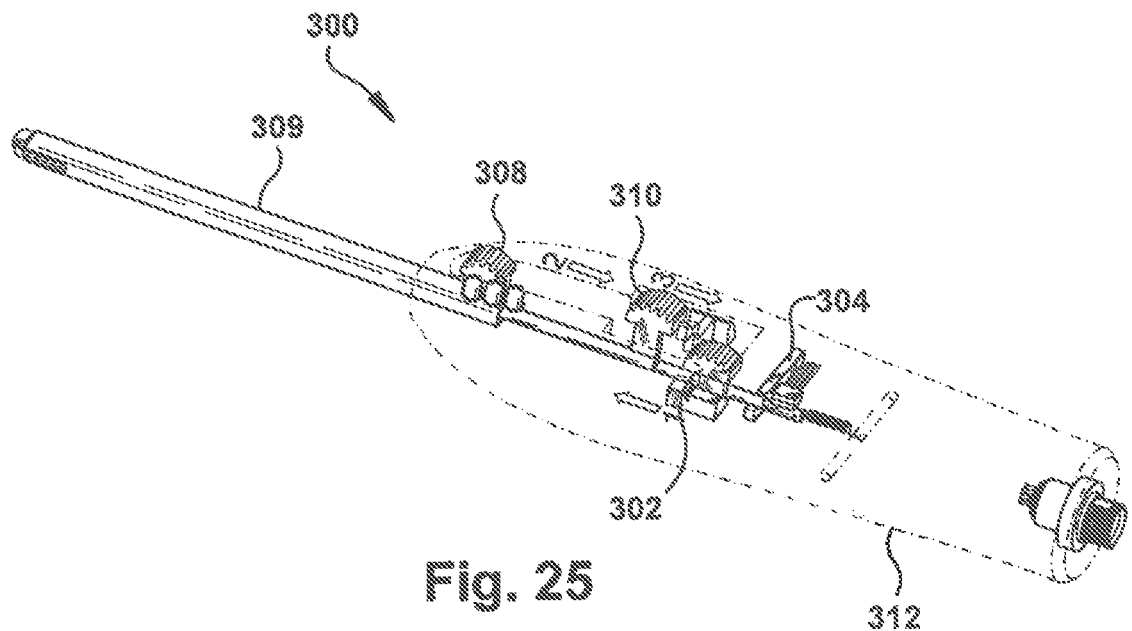

FIG. 24 illustrates insertion tool 300 during the pre-deployment stage and FIG. 25 illustrates insertion tool 300 during the sensing stage. At both these stages, slider for anchor deployment 302 is in a proximal position in handle body 312, anchor sensor lock 304 is in a locked configuration, slider 308 for sheath 309 is in a distal position in handle body 312, slider for microstimulator release 310 is locked and in a distal position in handle body 312. During the sensing stage illustrated in FIG. 25, sensing can be performed by electrodes of the microstimulator or by electrodes on the bottom surface of sheath 309.

Figure 26:
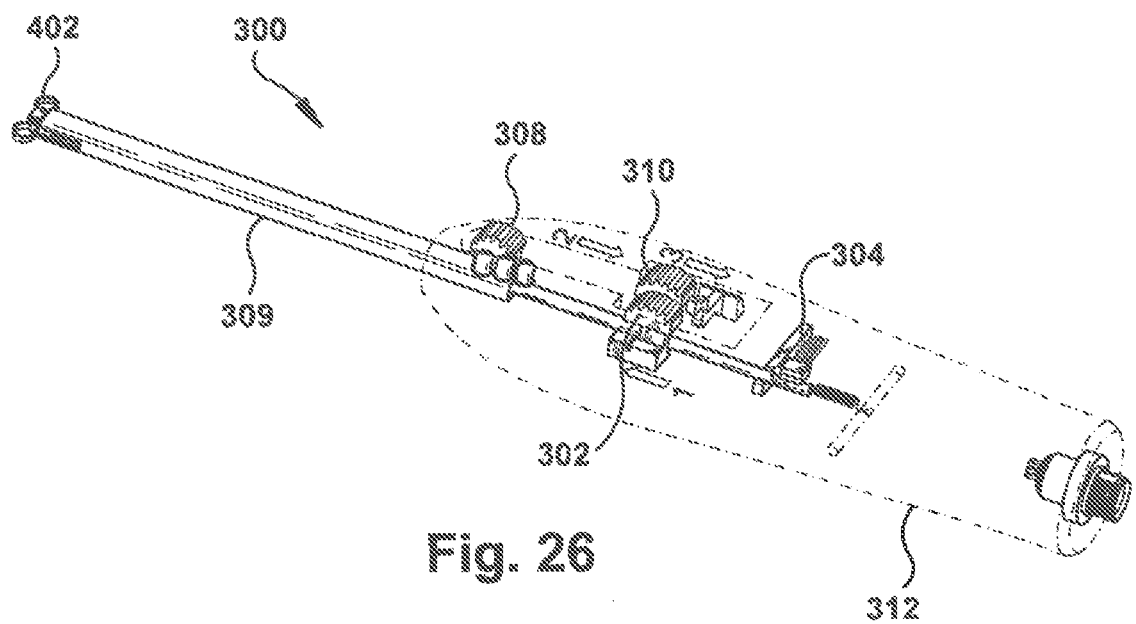
Figure 27:
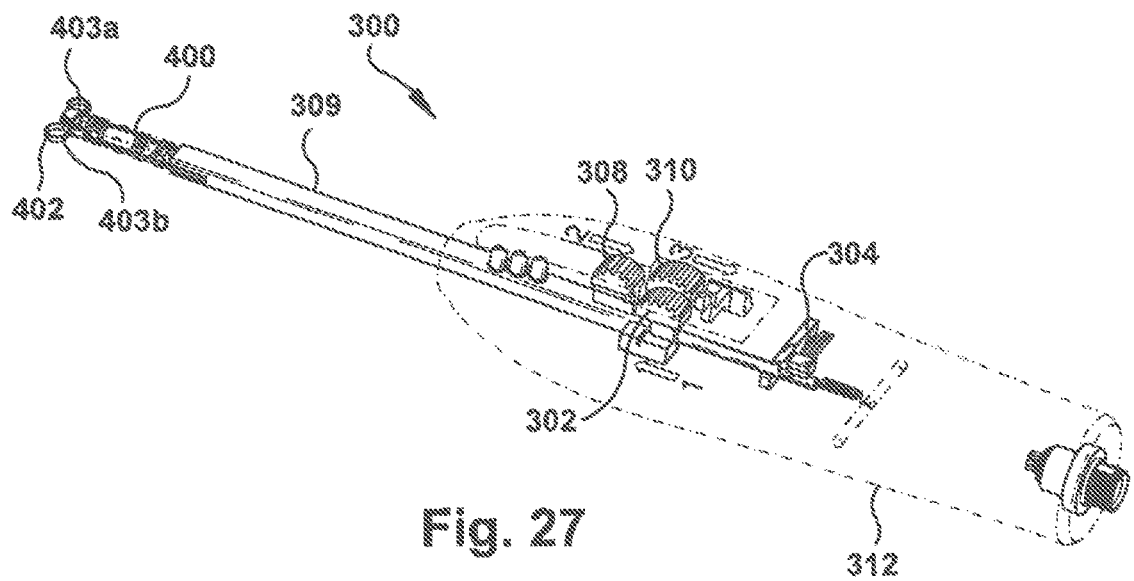

FIG. 26 illustrates insertion tool 300 during the anchor deployment stage. At this stage, the slider for anchor deployment 302 is urged distally to deploy a fixation member 402 of the microstimulator. FIG. 27 illustrates insertion tool 300 during the anchor release stage. At this stage, slider 308 for sheath 309 is pulled back proximally to expose microstimulator 400 and slider for anchor deployment 302 is urged distally to fully deploy fixation member 402. Arms 403a and 403b of fixation member 402 are spring loaded such that they spring outward once sheath 309 is pulled back proximally to expose arms 403a and 403b.

Figure 28:
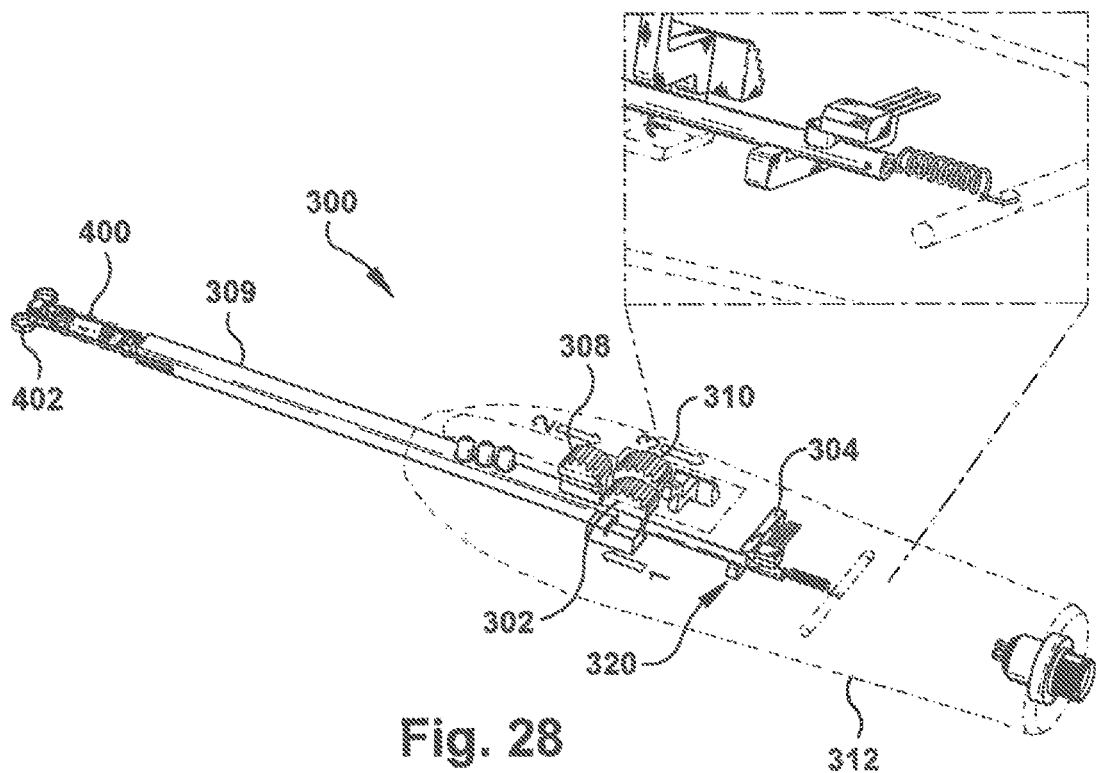

FIG. 28 illustrates insertion tool 300 at the anchor confirmation stage. At this stage, anchor sensor lock 304 is in an unlocked configuration. Unlocking shaft 320 within handle body 312 activates a spring to place a given load on fixation member 402 to ensure it is properly secured. Feedback received from the anchor feedback sensor 306 (which can be a Hall effect sensor) can be sent to an external processor via an electrical connector or a separate unit plugged into the back of insertion tool 300 and then sent back to LED indicators.

Figure 29:
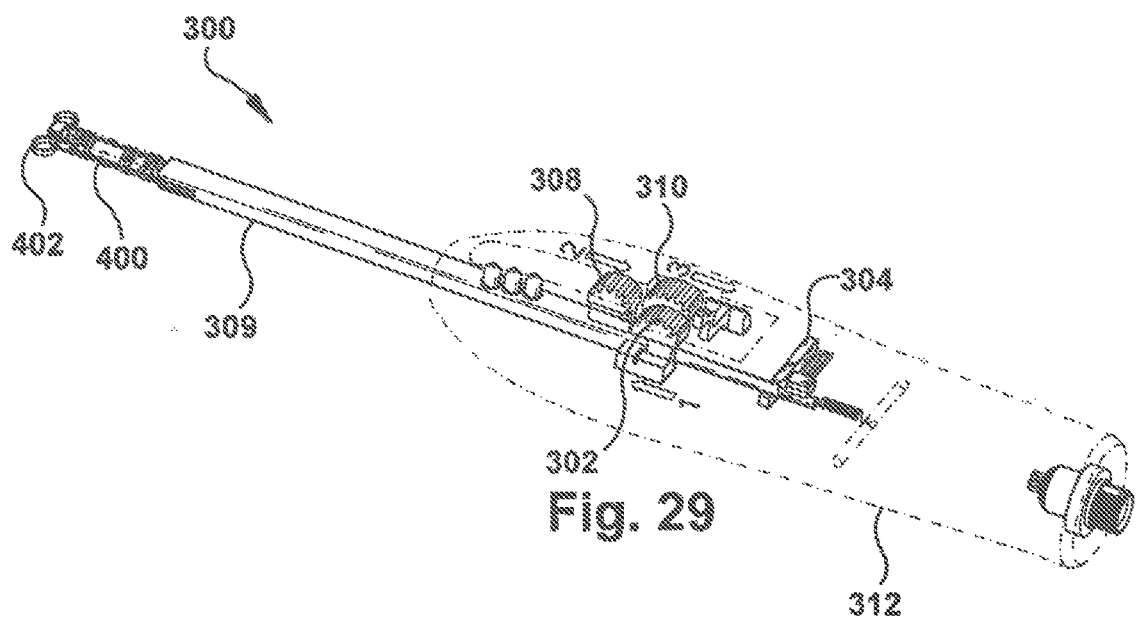
Figure 30:
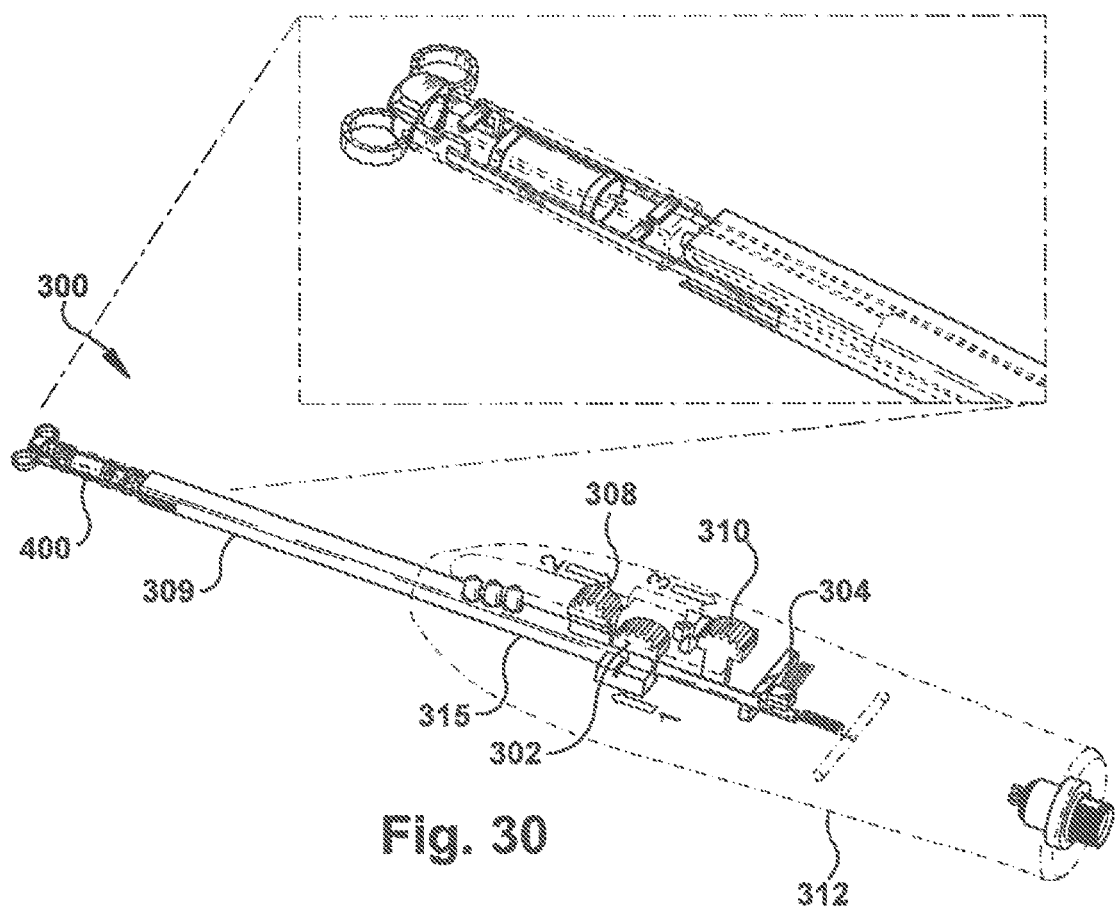

FIGS. 29 and 30 illustrate insertion tool 300 during the microstimulator 400 release stage. At this stage, slider for microstimulator release 310 is unlocked, as illustrated in FIG. 29 and pulled back proximally, as illustrated in FIG. 30 to release microstimulator 400. Shaft 315, attached to slider for microstimulator release 310, is retracted allowing an inner shaft 320 to spring open off a feature, such as, for example, a trailer hitch, on the microstimulator 400. In certain embodiments, prior to finalizing the implant of the microstimulator by "undocking" the microstimulator from the delivery tool and retracting the delivery tool, the microstimulator can be programmed to deliver stimulation at a predetermined intensity deemed to have therapeutic benefits as described above. For many patients, the stimulation is either imperceptible or produces paresthesia. However, some patients may find the stimulation to be uncomfortable and/or even painful. By inquiring about the sensation perceived by the patient before "undocking" the microstimulator from the delivery tool, the probability of prescribed therapy compliance is increased and that of any adverse effects due to stimulation is decreased.

Embodiments as disclosed herein are directed to improving pelvic floor dysfunction and pain, such as peripheral nerve pain. Pelvic floor dysfunction includes bladder dysfunction, bowel dysfunction, and fecal incontinence. Bladder dysfunction includes urinary incontinence such as urge incontinence, mixed incontinence, and overflow incontinence. Bladder dysfunction also includes "voiding dysfunction," which refers to urinary incontinence, urinary retention conditions, high urinary frequency, high or low frequency of voiding, symptoms of bladder/pelvic pressure/pain, detrusor hyperrflexia, and voiding disorders caused by nerve damage, including interstitial cystitis. Overactive bladder is a specific type of voiding dysfunction that includes any or all of the following symptoms: urinary frequency (bothersome urination eight or more times a day or two more times at night), urinary urgency (the sudden, strong need to urinate immediately), urge incontinence (leakage or gushing of urine that follows a sudden strong urge) and nocturia (awakening two or more times at night to urinate). Bowel dysfunction includes constipation (including idiopathic constipation), fecal incontinence, and problems with fecal movement, voiding and containment. Improving pelvic floor dysfunction can also include modulating contraction of the pelvic floor or "pelvic diaphragm." Over time, therapy may cause contractions that restore the strength of pelvic organs and muscles, which may be a goal of the therapy. Stimulation induced modulation of pelvic floor, sphincter or other targets can alleviate or eliminate many symptoms of urinary/fecal disorders As state above, embodiments as disclosed herein differ from other methods of treating pelvic floor dysfunction, such as an overactive bladder. SNS and PTNS involve placing an electrode below deep fascia in close proximity to the target nerve such as the sacral nerve or the tibial nerve. As such, the electrodes have a greater probability of recruiting the respective target nerve and also require less energy to provide a therapy signal to the target nerve since the electrodes are positioned close to the target nerve. However, SNS requires invasive surgery such as dissecting the lumbodorsal fascia and separating the underlying paravertebral muscles to access the sacral nerve. In PTNS, a needle electrode is inserted across the cutaneous, superficial and deep tissue into the tibial nerve. Since the needle is not insulated, it stimulates all layers from the dermis down to the tibial nerve simultaneously. Cases have been reported where the intensity of the electrical signal delivered by the electrode is too high at the needle site prior to reaching the recommended therapeutic threshold as indicated by a "toe twitch" in the patient. Also, as an in-office procedure needed chronically, the personal burden is such that many patients stop the therapy before achieving the full benefit possible. Transcutaneous tibial nerve stimulation is less invasive than SNS and PTNS but is challenging in its own respect. For example, the variability of distance from skin to tibial nerve is much greater than deep fascia to tibial nerve both from patient to patient and within a given patient should they have fluctuations in their weight or fluid retention. Also, the reusable electrode placement on the skin is subjectively done by the patient and therefore variable in location and robustness of interface (e.g. hair interferes conduction of stimulation) from session to session and patient to patient. In addition, sensory fibers in the skin closest to the transcutaneous electrodes provide a level of discomfort with the stimulation, variable from patient to patient, which could limit the level of stimulation to less than a therapeutic level. Embodiments of devices and methods as described herein provide a minimally invasive yet targeted and efficacious form of therapy for improving pelvic floor dysfunction.

Each of the disclosed aspects and embodiments of the present disclosure may be considered individually or in combination with other aspects, embodiments, and variations of the disclosure. Unless otherwise specified, none of the steps of the methods of the present disclosure are confined to any particular order of performance.

What is claimed is:

1. A method of improving pelvic floor dysfunction in a patient suffering therefrom comprising:

inserting an electrical microstimulator having a re-deployable fixation member through skin of the patient's leg;
advancing the electrical microstimulator through the skin along tissue of a surgical pathway to a first implant site that is above deep fascia and below the skin and that is adjacent to a nerve associated with pelvic floor function;
delivering an electrical signal to the nerve;
determining activation of the nerve by delivery of the electrical signal;
anchoring the electrical microstimulator via the re-deployable fixation member to the first implant site upon a determination of activation of the nerve;
confirming activation of the nerve after anchoring the electrical microstimulator to the first implant site;
identifying the first implant site as a target implant site upon confirmation of activation of the nerve at the first implant site; and
delivering a therapeutic electrical signal to the nerve from the target implant site.

2. The method of 1, further comprising:
releasing the re-deployable fixation member from the first implant site upon non-confirmation of activation of the nerve;
re-positioning the electrical microstimulator to a second implant site;
delivering another electrical signal to the nerve;
determining activation of the nerve by delivery of the another electrical signal;
anchoring the electrical microstimulator via the re-deployable fixation member to the second implant site upon a determination of activation of the nerve;
confirming activation of the nerve after anchoring the electrical microstimulator to the second implant site;
identifying the second implant site as the target implant site upon confirmation of activation of the nerve at the second implant site; and
delivering the therapeutic electrical signal to the nerve from the target implant site.

3. The method of claim 1, wherein determining if the electrical signal activates the nerve comprises:
delivering a stimulating signal to the nerve as the electrical microstimulator is advanced along the surgical pathway, the stimulating signal applied by a stimulating electrode disposed on the electrical microstimulator or a delivery tool carrying the electrical microstimulator; and
sensing an evoked electrical signal in response to the stimulation signal thereby indicating activation of the nerve.

4. The method of claim 3, wherein the evoked electrical signal is an electromyogram (EMG) signal, an electroneurogram (ENG) signal, a trigeminal somatosensory evoked potential (TSEP), an evoked muscle action potential (EMAP) or an electrically evoked compound action potential (ECAP).

5. The method of claim 3, wherein sensing an evoked electrical signal comprises placing a sensor on the patient's foot and continuously measuring EMG activity of a muscle of the patient's foot innervated by the nerve as the electrical microstimulator is advanced along the surgical pathway and the stimulation signal is delivered to the nerve by the stimulating electrode.

6. The method of claim 3, wherein identifying the first implant site as the target implant site comprises detecting a maxima in the evoked electrical signal, the maxima being reached when application of a lowest amplitude of the delivered stimulation signal to the nerve elicits an evoked electrical signal.

7. The method of claim 6, further comprising measuring an impedance of tissue along the surgical pathway to ensure the delivery tool maintains contact with the tissue along the surgical pathway and does not penetrate into the deep fascia.

8. The method of claim 6, wherein the delivery tool comprises:
an interior chamber comprising a first spring and a second spring that is located proximal to the first spring, the first and second springs having different spring constant values;
a rod slidably extending through the inner housing and in contact with the first and second spring, the rod comprising a fascia detection indicator and an anchor verification indicator that is located proximal to the fascia detection indicator; and
a detection window in fluid communication with the interior chamber and longitudinally aligned with the fascia detection indicator and anchor verification indicator.

9. The method of claim 8, further comprising:
inserting the delivery tool along the surgical pathway, wherein contact with the deep fascia causes the first spring to compress and urge fascia indicator proximally to the detection window and sufficient anchoring of the electrical microstimulator causes the anchor verification indicator to remain in place when the electrical microstimulator is retracted proximally.

10. The method of claim 1, wherein the electrical microstimulator is advanced via a delivery tool, the delivery tool having a flexible, deflectable and/or blunt tip such that the delivery tool is deflected by the deep fascia to remain above the deep fascia.

11. The method of claim 10, further comprising:
verifying anchoring of the electrical microstimulator at the target implant site by retracting the delivery tool proximally to determine if the re-deployable fixation member disengages from the target implant site or by using a Hall sensor with a spring.

12. The method of claim 1, wherein the electrical microstimulator is pre-programmed with a plurality of stimulation protocols each having at least one pre-determined stimulation parameter that is known to have therapeutic benefit in improving pelvic floor dysfunction.

13. The method of claim 1, wherein the electrical microstimulator comprises:
a microstimulator body having a longitudinal axis extending therethrough and having a top surface, a bottom surface, a first lateral surface, a second lateral surface, a proximal end, and a distal end;
an independently programmable electrode on the top surface of the microstimulator body;
an independently programmable electrode on the bottom surface of the microstimulator body; and wherein
the re-deployable fixation member is disposed on the microstimulator body.

14. The method of claim 13, wherein the re-deployable fixation member comprises a first re-deployable fixation member disposed on the first lateral surface of the microstimulator body and a second re-deployable fixation member disposed on the second lateral surface of the microstimulator body, the first and second re-deployable fixation members disposed parallel to the longitudinal axis of the microstimulator body in a non-deployed configuration.

15. The method of claim 1, wherein a distal end of the microstimulator is blunt, wedge-shaped, round, asymmetrical, trowel shaped, or toboggan-shaped.

16. The method of claim 1, wherein the electrical microstimulator comprises:
a microstimulator body having a top surface, a bottom surface, a first lateral surface, a second lateral surface, a proximal end, and a distal end;
at least two independently programmable electrodes on the bottom surface of the microstimulator body; and
wherein the re-deployable fixation member is disposed on the microstimulator body.

17. The method of claim 1, wherein the pelvic floor dysfunction is an overactive bladder.

18. The method of claim 1, wherein confirming activation of the nerve comprises:
delivering a stimulating signal to the nerve, the stimulating signal applied by a stimulating electrode disposed on the electrical microstimulator or a delivery tool carrying the electrical microstimulator; and
sensing an evoked electrical signal in response to the stimulation signal thereby indicating confirmation of activation of the nerve.

19. The method of claim 1, wherein anchoring the re-deployable fixation member of the electrical microstimulator to the target implant site comprises anchoring the re-deployable fixation member above deep fascia and not to a layer of deep fascia.

* * * * *